United States Patent
McPherson et al.

(10) Patent No.: US 11,229,676 B2
(45) Date of Patent: *Jan. 25, 2022

(54) METHODS AND COMPOSITIONS FOR DIAGNOSIS AND PROGNOSIS OF RENAL INJURY AND RENAL FAILURE

(71) Applicants: ASTUTE MEDICAL, INC., San Diego, CA (US); UNIVERSITY OF PITTSBURGH—OF THE COMMONWEALTH SYSTEM OF HIGHER EDUCATION, Pittsburgh, PA (US)

(72) Inventors: Paul McPherson, Encinitas, CA (US); John A. Kellum, Pittsburgh, PA (US)

(73) Assignee: ASTUTE MEDICAL, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/422,520

(22) Filed: May 24, 2019

(65) Prior Publication Data

US 2019/0381130 A1    Dec. 19, 2019

Related U.S. Application Data

(63) Continuation of application No. 15/101,118, filed as application No. PCT/US2014/068337 on Dec. 3, 2014, now Pat. No. 10,300,108.

(60) Provisional application No. 61/911,406, filed on Dec. 3, 2013.

(51) Int. Cl.
| | | |
|---|---|---|
| A61K 38/13 | (2006.01) | |
| G01N 33/68 | (2006.01) | |
| A61K 45/06 | (2006.01) | |
| A61K 38/17 | (2006.01) | |
| A61K 38/55 | (2006.01) | |
| A61K 31/436 | (2006.01) | |
| A61K 31/357 | (2006.01) | |
| A61K 31/366 | (2006.01) | |
| A61K 31/437 | (2006.01) | |
| A61K 31/453 | (2006.01) | |
| A61K 31/55 | (2006.01) | |
| A61K 31/585 | (2006.01) | |

(52) U.S. Cl.
CPC ............ *A61K 38/13* (2013.01); *A61K 31/357* (2013.01); *A61K 31/366* (2013.01); *A61K 31/436* (2013.01); *A61K 31/437* (2013.01); *A61K 31/453* (2013.01); *A61K 31/55* (2013.01); *A61K 31/585* (2013.01); *A61K 38/1754* (2013.01); *A61K 38/55* (2013.01); *A61K 45/06* (2013.01); *G01N 33/6893* (2013.01); *G01N 2333/4745* (2013.01); *G01N 2333/8146* (2013.01); *G01N 2800/347* (2013.01); *G01N 2800/50* (2013.01)

(58) Field of Classification Search
None
See application file for complete search history.

(56) References Cited

U.S. PATENT DOCUMENTS

| | | |
|---|---|---|
| 5,324,634 A | 6/1994 | Zucker |
| 5,480,792 A | 1/1996 | Buechler |
| 5,525,524 A | 6/1996 | Buechler et al. |
| 5,571,698 A | 11/1996 | Ladner et al. |
| 5,631,171 A | 5/1997 | Sandstrom et al. |
| 5,679,526 A | 10/1997 | Buechler et al. |
| 5,824,799 A | 10/1998 | Buechler et al. |
| 5,851,776 A | 12/1998 | Valkirs |
| 5,885,527 A | 3/1999 | Buechler |
| 5,922,615 A | 7/1999 | Nowakowski et al. |
| 5,939,272 A | 8/1999 | Buechler et al. |
| 5,947,124 A | 9/1999 | Buechler et al. |
| 5,955,377 A | 9/1999 | Maul et al. |
| 5,985,579 A | 11/1999 | Buechler et al. |
| 6,019,944 A | 2/2000 | Buechler |
| 6,057,098 A | 5/2000 | Buechler et al. |
| 6,113,855 A | 9/2000 | Buechler et al. |

(Continued)

FOREIGN PATENT DOCUMENTS

| | | |
|---|---|---|
| JP | 2003-081838 | 3/2003 |
| JP | 2014234388 | 12/2014 |

(Continued)

OTHER PUBLICATIONS

Bennett et al., "Chronic cyclosporine nephropathy: the Achilles' heel of immunosuppressive therapy", Kidney Int. Oct. 1996;50(4): 1089-100.*

Healy et al., "Apoptosis and necrosis: mechanisms of cell death induced by cyclosporine A in a renal proximal tubular cell line" Kidney Int. Dec. 1998;54(6): 1955-66.*

(Continued)

*Primary Examiner* — Maury A Audet

(74) *Attorney, Agent, or Firm* — Womble Bond Dickinson (US) LLP

(57) ABSTRACT

It is an object of the present invention to provide methods and compositions for protection of subjects from acute kidney injury by treating the subject with compounds that modulate the cell cycle. Modulating the cell cycle can comprise inducing $G_0/G_1$ cell cycle arrest, and/or inducing cell cycle progression. As demonstrated below, even a single administration of a compound which induces $G_0/G_1$ cell cycle arrest can protect subjects from AKI, and may be used prophylactically in advance of, or as a treatment following, various treatments or conditions that are known to be injurious to the kidney, followed optionally by release of the arrest. Once AKI is established, cell cycle progression can be induced to increase replacement of lost and damaged cells.

16 Claims, 11 Drawing Sheets

(56) References Cited

U.S. PATENT DOCUMENTS

| | | | |
|---|---|---|---|
| 6,140,045 | A | 10/2000 | Wohlstadter et al. |
| 6,143,576 | A | 11/2000 | Buechler |
| 8,778,615 | B2 | 7/2014 | Anderberg et al. |
| 8,993,250 | B2 | 3/2015 | Anderberg et al. |
| 9,029,093 | B2 | 5/2015 | Anderberg et al. |
| 9,057,735 | B2 | 6/2015 | Anderberg et al. |
| 9,229,010 | B2 | 1/2016 | Anderberg et al. |
| 9,360,488 | B2 | 5/2016 | Anderburg et al. |
| 9,459,261 | B2 | 10/2016 | Anderberg et al. |
| 9,696,322 | B2 | 7/2017 | Anderberg et al. |
| 9,784,750 | B2 | 10/2017 | Anderberg et al. |
| 9,822,172 | B2 | 11/2017 | Vijayendran et al. |
| 9,879,091 | B2 | 1/2018 | Vijayendran et al. |
| 10,300,108 | B2 | 5/2019 | McPherson et al. |
| 2003/0186308 | A1 | 10/2003 | Young et al. |
| 2004/0126767 | A1 | 7/2004 | Anderberg et al. |
| 2004/0253637 | A1 | 12/2004 | Buechler |
| 2005/0084880 | A1 | 4/2005 | Duman et al. |
| 2006/0240437 | A1 | 10/2006 | Krolewski et al. |
| 2006/0257903 | A1 | 11/2006 | Akil et al. |
| 2007/0087387 | A1 | 4/2007 | Devarajan et al. |
| 2007/0184439 | A1 | 8/2007 | Guilford et al. |
| 2007/0248989 | A1 | 10/2007 | Devarajan |
| 2007/0249002 | A1 | 10/2007 | Hu et al. |
| 2008/0038192 | A1 | 2/2008 | Gervais |
| 2008/0090759 | A1 | 4/2008 | Kokenyesi et al. |
| 2008/0133141 | A1 | 6/2008 | Frost |
| 2008/0153092 | A1 | 6/2008 | Kienle et al. |
| 2008/0254483 | A1 | 10/2008 | Darbouret et al. |
| 2009/0130693 | A1 | 5/2009 | Bassi et al. |
| 2009/0179287 | A1 | 7/2009 | Inaba |
| 2009/0197287 | A1 | 8/2009 | Hu et al. |
| 2009/0220526 | A1 | 9/2009 | Hamid |
| 2010/0267061 | A1 | 10/2010 | Hsieh et al. |
| 2011/0195429 | A1 | 8/2011 | Anderberg et al. |
| 2012/0156701 | A1 | 6/2012 | Anderburg et al. |
| 2012/0208717 | A1 | 8/2012 | Hu et al. |
| 2012/0283128 | A1 | 11/2012 | Anderburg et al. |
| 2013/0157881 | A1 | 6/2013 | Anderberg et al. |
| 2013/0210043 | A1 | 8/2013 | Anderberg et al. |
| 2014/0213477 | A1 | 7/2014 | Anderberg et al. |
| 2014/0323594 | A1 | 10/2014 | Anderberg et al. |
| 2014/0343600 | A1 | 11/2014 | Leschinsky |
| 2014/0377777 | A1 | 12/2014 | Anderberg et al. |
| 2016/0146832 | A1 | 5/2016 | Chawla et al. |
| 2017/0248613 | A1 | 8/2017 | Anderberg et al. |
| 2018/0074054 | A1 | 3/2018 | McPherson et al. |
| 2019/0263926 | A1 | 8/2019 | McPherson et al. |

FOREIGN PATENT DOCUMENTS

| | | |
|---|---|---|
| WO | WO 2000/037944 | 6/2000 |
| WO | WO 2003/054004 | 7/2003 |
| WO | WO 2006/010529 | 2/2006 |
| WO | WO 2007/124331 | 11/2007 |
| WO | WO 2008/067065 | 6/2008 |
| WO | WO 2008/089994 | 7/2008 |
| WO | WO 2009/062520 | 5/2009 |
| WO | WO 2010/025424 | 3/2010 |
| WO | WO 2010/045714 | 4/2010 |
| WO | WO 2010/048346 | 4/2010 |
| WO | WO 2011/017614 | 2/2011 |
| WO | WO 2011/025917 | 3/2011 |
| WO | WO 2011/035323 | 3/2011 |
| WO | WO 2011/075744 | 6/2011 |
| WO | WO 2011/097539 | 8/2011 |
| WO | WO 2011/106746 | 9/2011 |
| WO | WO 2011/162821 | 12/2011 |
| WO | WO 2013/043310 | 3/2013 |
| WO | WO 2013/086359 | 6/2013 |
| WO | WO 2014/070935 | 5/2014 |
| WO | WO 2014/113558 | 7/2014 |
| WO | WO 2014/197729 | 12/2014 |
| WO | WO 2015/021308 | 2/2015 |
| WO | WO 2015/069880 | 5/2015 |
| WO | WO 2015/084939 | 6/2015 |
| WO | WO 2016/164854 | 10/2016 |
| WO | WO 2017/060525 | 4/2017 |
| WO | WO 2017/214203 | 12/2017 |
| WO | WO 2018/081578 | 5/2018 |
| WO | WO 2018/145117 | 8/2018 |
| WO | WO 2018/187453 | 10/2018 |
| WO | WO 2018/208684 | 11/2018 |

OTHER PUBLICATIONS

Kashani et al., "Discovery and validation of cell cycle arrest biomarkers in human acute kidney injury", Crit Care. Feb. 13, 2013;17(1):R25, pp. 1-12.*

Sabbahy et al., "Ischemic kidney injury and mechanisms of tissue repair", Wiley Interdiscip Rev Syst Biol Syst. Biol. Med Sep. 2011;3(5):1-18. Epub Dec. 31, 2010.*

Altom et al., "Optimizing enzyme-linked immunosorbent assays on automated 96-well plate robotic systems," Laboratory Robotics and Automation, 1990, 2(3):139-146—Abstract only.

Amemiya et al., "Insulin like growth factor binding protein-7 reduces growth of human breast cancer cells and xenografted tumors," Breast Cancer Res Treat, 2011, 126:373-384.

Bagshaw et al., "Urinary biomarkers in septic acute kidney injury," Intensive Care Med, 2007, 33:1285-1296.

Basu et al., "Identification of candidate serum biomarkers for severe septic shock-associated kidney injury via microarray," CritCare, 2011, 15:R273, 11 pp.

Caron et al., "Ischemic injury alters endothelial cell properties of kidney cortex: Stimulation of MMP-9," Exp Cell Res., 2005, 310:105-116.

Coca et al., "Biomarkers for the diagnosis and risk stratification of acute kidney injury: A systematic review," Kidney Int, 2008, 73:1008-1016.

Constantin et al., "Plasma neutrophil gelatinase-associated lipocalin is an early marker of acute kidney injury in adult critically ill patients: a prospective study," J Crit Care, 2010, 25:176.e1-176.e6.

Devarajan, "Update on Mechanisms of Ischemic Acute Kidney Injury," J Am Soc Nephrol, 2006, 17:1503-1520.

Fu et al., "Study on the expression of VEGF, MMP-2 and TIMP-2 in the progression of IgA nephropathy," J Clin Exp Pathol, Oct. 2008, 24(5):573-576—Abstract only.

Gocze et al., "Urinary Biomarkers TIMP-2 and IGFBP7 Early Predict Acute Kidney Injury after Major Surgery," PLoS ONE, Mar. 23, 2015, DOI:10.1371 /journal.pone.0120863, pp. 1-11.

Han et al., "Urinary biomarkers in the early diagnosis of acute kidney injury," Kidney Int, 2008, 73:863-869.

Hanley et al., "The Meaning and Use of the Area under a Receiver Operating Characteristic (ROC) Curve," Radiology, Apr. 1982, 143:29-36.

Hoste et al., "RIFLE criteria for acute kidney injury are associated with hospital mortality in critically ill patients: a cohort analysis.," Crit Care, 2006, 10(3):R73, 10 pp.

Humphreys et al., "Mesenchymal Stem Cells in Acute Kidney Injury," Annu Rev Med, 2008, 59:311-325.

Keightley, "A comparison of manual and robotic pipetting for plate-based assays," Laboratory Practice, 1989, 38(10):53-55—Abstract only.

Kierdorf et al., "Continuous Renal Replacement Therapies Versus Intermittent Hemodialysis in Acute Renal Failure: What do we know?," American Journal of Kidney Diseases, Nov. 1996, 28(5)(Supp3):S90-S96.

Kingsmore et al., "Multiplexed protein profiling on antibody-based microarrays by rolling circle amplification," Current Opin Biotechnol, 2003, 14:74-81.

Kutsukake et al., "Circulating IGF-binding protein 7 (IGFBP7) levels are elevated in patients with endometriosis or undergoing diabetic hemodialysis," Reproductive Biology and Endocrinology, 2008, 6:54, 6 pp.

Lan, "Clinical significance of determination of serum hyaluronic acid, type III procollagen, collagen IV and laminin in patients with nephropathy," J Guangxi Med Univ, Oct. 2002, 19(5):655-656— English translation of abstract only.

(56) References Cited

OTHER PUBLICATIONS

López-Bermejo et al., "Generation of Anti-Insulin-Like Growth Factor-Binding Protein-Related Protein 1 (IGFBP-rP1/MAC25) Monoclonal Antibodies and Immunoassay: Quantification of IGFBP-rP1 in Human Serum and Distribution in Human Fluids and Tissues," J Clin Endocrinol Metab, 2003, 88(7):3401-3408.

Matousovic et al., "IgA-containing immune complexes in the urine of IgA nephropathy patients," Nephrol Dial Transplant, 2006, 21:2478-2484.

Mazanowska et al., "Imbalance of Metallaproteinase/Tissue Inhibitors of Metalloproteinase System in Renal Transplant Recipients With Chronic Allograft Injury," Transplant Proc, 2011, 43(8):3000-3003.

Meersch et al., "Urinary TIMP-2 and IGFBP7 as Early Biomarkers of Acute Kidney Injury and Renal Recovery following Cardiac Surgery," PLoS One, Mar. 2014; 9(3):e93460, 9 pp.

Nejat et al., "Urinary cystatin C is diagnostic of acute kidney injury and sepsis, and predicts mortality in the intensive care unit," Crit Care, 2010;14:R85, 13 pp.

Nguyen et al., "Biomarkers for the early detection of acute kidney injury," Pediatr Nephrol, 2008, 23:2151-2157.

Pajenda et al., "NephroCheck data compared to serum creatinine in various clinical settings," BMC Nephrology, 2015, 16:206, 7 pp.

Parikh et al., "New biomarkers of acute kidney injury," Crit Care Med, 2008, 36(4 Suppl):S159-S165.

Shek et al., "Robotic enzyme-linked immunosorbent assay (ELISA) system for rodent serology: modifications to enhance capacity, throughput and sensitivity," Proc Int Symp Lab Autom Rob, Conference 1992, pp. 282-298—Abstract only.

Siew et al., "Biological Markers of Acute Kidney Injury," J Am Soc Nephrol, 2011, 22:810-820.

Stampfer et al., "Risk Factor Criteria," Circulation, 2004, 109(Suppl IV):IV-3-IV-5.

Stenvinkel et al., "High Serum Hyaluronan Indicates Poor Survival in Renal Replacement Therapy," Am J Kidney Dis, Dec. 1999, 34(6):1083-1088.

Su et al., "Diagnostic value of urine sTREM-1 for sepsis and relevant acute kidney injuries: a prospective study," Crit Care, 2011, 15:R250, 10 pp.

Tan et al., "The level of urinary secretory immunoglobulin A (sIgA) of patients with IgA nephropathy is elevated and associated with pathological phenotypes," Clin Exp Immunol, 2009, 156:111-116.

Thiele et al., "AKI Associated with Cardiac Surgery," Clin J Ann Soc Nephrol, 2015, 10:500-514.

Waikar et al., "Imperfect Gold Standards for Kidney Injury Biomarker Evaluation," J Am Soc Nephrol, Jan. 2012, 23(1):13-21.

Wetz et al., "Quantification of urinary TIMP-2 and IGFBP-7: an adequate diagnostic test to predict acute kidney injury after cardiac surgery?," Critical Care, 2015, 19:3, 7 pp.

Yan et al., "Expression of MMP-2 and TIMP-1 in Renal Tissue of Patients with Chronic Active Antibody-Mediated Renal Graft Rejection," Diagn Pathol, 2012, 7:141, 6 pp.

Yang et al., "Remote Ischemic Preconditioning for Prevention of Acute Kidney Injury: A Meta-analysis of Randomized Controlled Trials," Am J Kidney Dis, 2014, 64(4):574-583.

Zhang et al., "The level of serum secretory IgA of patients with IgA nephropathy is elevated and associated with pathological phenotypes," Nephrol Dial Transplant, 2008, 23:207-212.

Office Action dated Feb. 1, 2018, in Chinese Application (No. 2014800736390).

Aregger et al., "Identification of IGFBP-7 by urinary proteomics as a novel prognostic marker in early acute kidney injury," Kidney International, 2014, 85(4):909-919.

Bagshaw et al., "A multi-centre evaluation of the RIFLE criteria for early acute kidney injury in critically ill patients," Nephrol Dial Transplant, 2008, 23(4):1203-1210.

Bellomo et al., "Acute renal failure—definition, outcome measures, animal models, fluid therapy and information technology needs: the Second International Consensus Conference of the Acute Dialysis Quality Initiative (ADQI) Group," Crit Care, 2004, 8(4):R204-R212.

Bennett et al., "Chronic cyclosporine nephropathy: The Achilles' heel of immunosuppressive therapy," Kidney Int., 1996, 50(4):1089-1100.

Chawla et al., "Identifying critically ill patients at high risk for developing acute renal failure: A pilot study," Kidney Int., 2005, 68(5):2274-2280.

Chertow et al., "Acute Kidney Injury, Mortality, Length of Stay, and Costs in Hospitalized Patients," J Am Soc Nephrol, 2005, 16(11):3365-3370.

Cwirla et al., "Peptides on phage: A vast library of peptides for identifying ligands," Proc Natl Acad Sci USA, 1990, 87(16):6378-6382.

Devlin et al., "Random Peptide Libraries: A Source of Specific Protein Binding Molecules," Science, Jul. 27, 1990, 249(A967):404-406.

Fischer et al., "A readers' guide to the interpretation of diagnostic test properties: clinical example of sepsis," Intensive Care Med, 2003, 29(7):1043-1051.

Goldstein et al., "Renal Angina," Clin J Am Soc Nephrol, 2010, 5(5):943-949.

Healy et al., "Apoptosis and necrosis: Mechanisms of cell death induced by cyclosporine A in a renal proximal tubular cell line," Kidney Int, 1998, 54(6):1955-1966.

Kamimoto et al., "Hepatocyte growth factor prevents multiple organ injuries in endotoxemic mice through a heme oxygenase-1-dependent mechanism," Biochem Biophys Res Commun, 2009, 380(2):333-337.

Kashani et al., "Discovery and validation of cell cycle arrest biomarkers in human acute kidney injury," Crit Care, 2013, 17(1):R25. doi: 10.1186/cc12503.

Kellum, "Acute kidney injury," Crit Care Med, 2008, 36(4 Suppl):S141-S145.

Kunugi et al., "Inhibition of matrix metalloproteinases reduces ischemia-repertusion acute kidney injury," Lab Invest, 2011, 91(2):170-180.

Lassnigg et al., "Minimal Changes of Serum Creatinine Predict Prognosis in Patients after Cardiothoracic Surgery: A Prospective Cohort Study," J Am Soc Nephrol, 2004, 15(6):1597-1605.

McCullough et al., "Contrast-Induced Nephropathy (CIN) Consensus Working Panel: Executive Summary," Rev Cardiovasc Med, 2006, 7(4):177-197.

Mehran et al., A Simple Risk Score for Prediction of Contrast-Induced Nephropathy After Percutaneous Coronary Intervention: Development and Initial Validation, J Am Coll Cardiol, 2004, 44(7):1393-1399.

Mehta et al., "Acute Kidney Injury Network: report of an initiative to improve outcomes in acute kidney injury," Crit Care, 2007, 11(2):R31 (8 pages).

Nelson et al., "A computer program for calculating antibody affinity constants," Comput Methods Programs Biomed, 1988, 27(1):65-68.

Praught et al., "Are small changes in serum creatinine an important risk factor?," Curr Opin Nephrol Hypertens, 2005, 14(3):265-270.

Ricci et al., "The RIFLE criteria and mortality in acute kidney injury: A systematic review," Kidney Int, 2008, 73:538-546.

Sabbahy et al., "Ischemic kidney injury and mechanisms of tissue repair," Wiley Interdiscip Rev Syst Biol Med, Sep. 30, 2011, 3(5):606-618.

Scott et al., Searching for Peptide Ligands with an Epitope Library, Science, Jul. 27, 1990, 249:386-390.

Thakar et al., "A Clinical Score to Predict Acute Renal Failure after Cardiac Surgery," J Am Soc Nephrol, 2005, 16:162-168.

Van Erp et al., "Application of a Sol Particle Immunoassay to the Determination of Affinity Constants of Monoclonal Antibodies," J Immunoassay, 1991, 12(3):425-443.

Ward et al., "Binding activities of a repertoire of single immunoglobulin variable domains secreted from *Escherichia coli*," Nature, Oct. 12, 1989, 341:544-546.

Wen et al., "One dose of cyclosporine A is protective at initiation of folic acid-induced acute kidney injury in mice," Nephrol Dial Transplant, 2012, 27:3100-3109.

(56) References Cited

OTHER PUBLICATIONS

Wijeysundera et al., "Derivation and Validation of a Simplified Predictive Index for Renal Replacement Therapy After Cardiac Surgery," JAMA, Apr. 25, 2007, 297:1801-1809.

Wilson et al., "Simplified conjugation chemistry for coupling peptides to F(ab') fragments: autologous red cell agglutination assay for HIV-1 antibodies," J Immunol Methods, 1994, 175:267-273.

Witzgall et al., "Localization of Proliferating Cell Nuclear Antigen, Vimentin, c-Fos, and Clusterin in the Postischemic Kidney: Evidence for a Heterogenous Genetic Response among Nephron Segments, and a Large Pool of Mitotically Active and Dedifferentiated Cells," J Clin Invest, May 1994, 93:2175-2188.

Yang et al., "Acute renal failure during sepsis: Potential role of cell cycle regulation," J Infect, 2009, 58:459-464.

Yarmush et al., "Coupling of antibody-binding fragments to solid-phase supports: site-directed binding of F(ab')$_2$ fragments," J Biochem Biophys Methods, 1992, 25:285-297.

Yasuda et al., "Insulin like growth factor-1 increases p21 expression and attenuates cisplatin-induced acute renal injury in rats," Clin Exp Nephrol, 2004, 8:27-35.

Yasuda et al., "Simvastatin improves sepsis-induced mortality and acute kidney injury via renal vascular effects," Kidney Int, May 2006, 69(9):1535-1542.

Extended European Search Report dated May 31, 2017, in EP application (No. 14868424).

International Preliminary Report on Patentability dated Jun. 16, 2016, in PCT/US2014/068337.

International Search Report and Written Opinion dated Feb. 26, 2015, in PCT/US2014/068337.

Official action dated Jun. 2, 2017, in Chinese Application (No. 2014800736390).

Official action dated Nov. 22, 2018, in European application (No. 14868424).

Official action dated Sep. 11, 2018, Japanese application (No. 2016-535047).

Official action dated May 7, 2019, in Japanese Application (No. 2016-535047).

Chindarkar et al., "Reference intervals of urinary acute kidney injury (AKI) markers [IGFBP7]•[TIMP2] in apparently healthy subjects and chronic comorbid subjects without AKI," Clinica Chimica Acta, 2016, 452:32-37.

He et al., "A research on serum, urine and tumor tissue hyaluronate assays for detecting malignant ovarian tumors," Zhonghua Fu Chan Ke Za Zhi, Mar. 1995, 30(3):161-163 (abstract only).

MacCallum et al., "Antibody-antigen Interactions: Contact Analysis and Binding Site Topography," J Mol Biol, 1996, 262:732-745.

Paul, "Fundamental Immunology," Third Edition, Structure and Function of Immunoglobulins, 1993, 8:292-295.

Vajdos et al., "Comprehensive Functional Maps of the Antigen-binding Site of an Anti-ErbB2 Antibody Obtained with Shotgun Scanning Mutagenesis," J Mol Biol, 2002, 320:415-428.

Wasung et al., "Biomarkers of renal function, which and when?," Clinica Chimica Acta, 2015, 438:350-357.

Wiki: "Chronic kidney disease", Jan. 3, 2020, Retrieved from the internet: URL:https://en.wikipedia.org/wiki/Chronic_kidney_disease [retrieved on Jan. 21, 2020].

Official action dated Mar. 9, 2020, in Indian application (No. 201627019122).

Official action dated Apr. 21, 2020, in European Application (No. 14868424).

Hoste et al., "Derivation and validation of cutoffs for clinical use of cell cycle arrest biomarkers," Nephrol Dial Transplant, 2014, 29:2054-2061.

Klein et al., "Renal replacement therapy in acute kidney injury," Medizinische Klinik, Urban & Vogel, Munich, May 2, 2017, 112(5):437-443 (in German, includes English abstract on p. 439; cited by EPO.

Ostermann et al., "Patient Selection and Timing of Continuous Renal Replacement Therapy," Blood Purif, 2016, 42:224-237.

Pilarczyk et al., "Tissue inhibitor of metalloproteinase 2 and insulin-like growth factor-binding protein 7, New biomarker combination for early recognition of acute kidney injury in cardiac surgery" Zeitschrift fur Herz-, Thorax- und Gefaesschirurgie, Mar. 1, 2017, 31:190-199 (in German, includes English abstract on p. 192; cited by EPO).

Venugopal et al., "Effect of Remote Ischemic Preconditioning on Acute Kidney Injury in Nondiabetic Patients Undergoing Coronary Artery Bypass Graft Surgery: A Secondary Analysis of 2 Small Randomized Trials," Am J Kidney Dis, Dec. 2010, 56(6-2):1043-1049.

Vijayan et al., "Clinical Use of the Urine Biomarker [TIMP-2]×[IGFBP7] for Acute Kidney Injury Risk Assessment," Am J Kidney Dis, 2016, 68(1):19-28.

Official action dated Oct. 20, 2020, in Japanese application (No. 2019-202233).

Extended European Search Report dated Dec. 3, 2020, in European application (No. EP18797960).

\* cited by examiner

METHODS AND COMPOSITIONS FOR DIAGNOSIS AND PROGNOSIS OF RENAL INJURY AND RENAL FAILURE

The present application claims priority to U.S. provisional patent application No. 61/911,406, filed Dec. 3, 2013, which is hereby incorporated by reference in its entirety.

STATEMENT REGARDING FEDERALLY SPONSORED RESEARCH

This invention was made with government support under National Heart Lung and Blood Institute (NHLBI) Grant Number R01HL080926. The government has certain rights in the invention.

BACKGROUND OF THE INVENTION

The following discussion of the background of the invention is merely provided to aid the reader in understanding the invention and is not admitted to describe or constitute prior art to the present invention.

The kidney is responsible for water and solute excretion from the body. Its functions include maintenance of acid-base balance, regulation of electrolyte concentrations, control of blood volume, and regulation of blood pressure. As such, loss of kidney function through injury and/or disease results in substantial morbidity and mortality. A detailed discussion of renal injuries is provided in Harrison's Principles of Internal Medicine, 17$^{th}$ Ed., McGraw Hill, New York, pages 1741-1830, which are hereby incorporated by reference in their entirety. Renal disease and/or injury may be acute or chronic. Acute and chronic kidney disease are described as follows (from Current Medical Diagnosis & Treatment 2008, 47$^{th}$ Ed, McGraw Hill, New York, pages 785-815, which are hereby incorporated by reference in their entirety): "Acute renal failure is worsening of renal function over hours to days, resulting in the retention of nitrogenous wastes (such as urea nitrogen) and creatinine in the blood. Retention of these substances is called azotemia. Chronic renal failure (chronic kidney disease) results from an abnormal loss of renal function over months to years".

Acute renal failure (ARF, also known as acute kidney injury, or AKI) is an abrupt (typically detected within about 48 hours to 1 week) reduction in glomerular filtration. This loss of filtration capacity results in retention of nitrogenous (urea and creatinine) and non-nitrogenous waste products that are normally excreted by the kidney, a reduction in urine output, or both. It is reported that ARF complicates about 5% of hospital admissions, 4-15% of cardiopulmonary bypass surgeries, and up to 30% of intensive care admissions. ARF may be categorized as prerenal, intrinsic renal, or postrenal in causation. Intrinsic renal disease can be further divided into glomerular, tubular, interstitial, and vascular abnormalities. Major causes of ARF are described in the following table, which is adapted from the Merck Manual, 17$^{th}$ ed., Chapter 222, and which is hereby incorporated by reference in their entirety:

| Type | Risk Factors |
| --- | --- |
| Prerenal | |
| ECF volume depletion | Excessive diuresis, hemorrhage, GI losses, loss of intravascular fluid into the extravascular space (due to ascites, peritonitis, pancreatitis, or burns), loss of skin and mucus membranes, renal salt- and water-wasting states |
| Low cardiac output | Cardiomyopathy, MI, cardiac tamponade, pulmonary embolism, pulmonary hypertension, positive-pressure mechanical ventilation |
| Low systemic vascular resistance | Septic shock, liver failure, antihypertensive drugs |
| Increased renal vascular resistance | NSAIDs, cyclosporines, tacrolimus, hypercalcemia, anaphylaxis, anesthetics, renal artery obstruction, renal vein thrombosis, sepsis, hepatorenal syndrome |
| Decreased efferent arteriolar tone (leading to decreased GLR from reduced glomerular transcapillary pressure, especially in patients with bilateral renal artery stenosis) | ACE inhibitors or angiotensin II receptor blockers |
| Intrinsic Renal | |
| Acute tubular injury | Ischemia (prolonged or severe prerenal state): surgery, hemorrhage, arterial or venous obstruction; Toxins: NSAIDs, cyclosporines, tacrolimus, aminoglycosides, foscarnet, ethylene glycol, hemoglobin, myoglobin, ifosfamide, heavy metals, methotrexate, radiopaque contrast agents, streptozotocin |
| Acute glomerulonephritis | ANCA-associated: Crescentic glomerulonephritis, polyarteritis nodosa, Wegener's granulomatosis; Anti-GBM glomerulonephritis: Goodpasture's syndrome; Immune-complex: Lupus glomerulonephritis, postinfectious glomerulonephritis, cryoglobulinemic glomerulonephritis |
| Acute tubulointerstitial nephritis | Drug reaction (eg, β-lactams, NSAIDs, sulfonamides, ciprofloxacin, thiazide diuretics, furosemide, phenytoin, allopurinol, pyelonephritis, papillary necrosis |

| Type | Risk Factors |
| --- | --- |
| Acute vascular nephropathy | Vasculitis, malignant hypertension, thrombotic microangiopathies, scleroderma, atheroembolism |
| Infiltrative diseases | Lymphoma, sarcoidosis, leukemia |
| Postrenal | |
| Tubular precipitation | Uric acid (tumor lysis), sulfonamides, triamterene, acyclovir, indinavir, methotrexate, ethylene glycol ingestion, myeloma protein, myoglobin |
| Ureteral obstruction | Intrinsic: Calculi, clots, sloughed renal tissue, fungus ball, edema, malignancy, congenital defects; Extrinsic: Malignancy, retroperitoneal fibrosis, ureteral trauma during surgery or high impact injury |
| Bladder obstruction | Mechanical: Benign prostatic hyperplasia, prostate cancer, bladder cancer, urethral strictures, phimosis, paraphimosis, urethral valves, obstructed indwelling urinary catheter; Neurogenic: Anticholinergic drugs, upper or lower motor neuron lesion |

In the case of ischemic ARF, the course of the disease may be divided into four phases. During an initiation phase, which lasts hours to days, reduced perfusion of the kidney is evolving into injury. Glomerular ultrafiltration reduces, the flow of filtrate is reduced due to debris within the tubules, and back leakage of filtrate through injured epithelium occurs. Renal injury can be mediated during this phase by reperfusion of the kidney. Initiation is followed by an extension phase which is characterized by continued ischemic injury and inflammation and may involve endothelial damage and vascular congestion. During the maintenance phase, lasting from 1 to 2 weeks, renal cell injury occurs, and glomerular filtration and urine output reaches a minimum. A recovery phase can follow in which the renal epithelium is repaired and GFR gradually recovers. Despite this, the survival rate of subjects with ARF may be as low as about 60%.

Acute kidney injury caused by radiocontrast agents (also called contrast media) and other nephrotoxins such as cyclosporine, antibiotics including aminoglycosides and anticancer drugs such as cisplatin manifests over a period of days to about a week. Contrast induced nephropathy (CIN, which is AKI caused by radiocontrast agents) is thought to be caused by intrarenal vasoconstriction (leading to ischemic injury) and from the generation of reactive oxygen species that are directly toxic to renal tubular epithelial cells. CIN classically presents as an acute (onset within 24-48 h) but reversible (peak 3-5 days, resolution within 1 week) rise in blood urea nitrogen and serum creatinine.

A commonly reported criteria for defining and detecting AKI is an abrupt (typically within about 2-7 days or within a period of hospitalization) elevation of serum creatinine. Although the use of serum creatinine elevation to define and detect AKI is well established, the magnitude of the serum creatinine elevation and the time over which it is measured to define AKI varies considerably among publications. Traditionally, relatively large increases in serum creatinine such as 100%, 200%, an increase of at least 100% to a value over 2 mg/dL and other definitions were used to define AKI. However, the recent trend has been towards using smaller serum creatinine rises to define AKI. The relationship between serum creatinine rise, AKI and the associated health risks are reviewed in Praught and Shlipak, *Curr Opin Nephrol Hypertens* 14:265-270, 2005 and Chertow et al, *J Am Soc Nephrol* 16: 3365-3370, 2005, which, with the references listed therein, are hereby incorporated by reference in their entirety. As described in these publications, acute worsening renal function (AKI) and increased risk of death and other detrimental outcomes are now known to be associated with very small increases in serum creatinine. These increases may be determined as a relative (percent) value or a nominal value. Relative increases in serum creatinine as small as 20% from the pre-injury value have been reported to indicate acutely worsening renal function (AKI) and increased health risk, but the more commonly reported value to define AKI and increased health risk is a relative increase of at least 25%. Nominal increases as small as 0.3 mg/dL, 0.2 mg/dL or even 0.1 mg/dL have been reported to indicate worsening renal function and increased risk of death. Various time periods for the serum creatinine to rise to these threshold values have been used to define AKI, for example, ranging from 2 days, 3 days, 7 days, or a variable period defined as the time the patient is in the hospital or intensive care unit. These studies indicate there is not a particular threshold serum creatinine rise (or time period for the rise) for worsening renal function or AKI, but rather a continuous increase in risk with increasing magnitude of serum creatinine rise.

One study (Lassnigg et all, J Am Soc Nephrol 15:1597-1605, 2004, hereby incorporated by reference in its entirety) investigated both increases and decreases in serum creatinine. Patients with a mild fall in serum creatinine of −0.1 to −0.3 mg/dL following heart surgery had the lowest mortality rate. Patients with a larger fall in serum creatinine (more than or equal to −0.4 mg/dL) or any increase in serum creatinine had a larger mortality rate. These findings caused the authors to conclude that even very subtle changes in renal function (as detected by small creatinine changes within 48 hours of surgery) seriously effect patient's outcomes. In an effort to reach consensus on a unified classification system for using serum creatinine to define AKI in clinical trials and in clinical practice, Bellomo et al., *Crit Care.* 8(4):R204-12, 2004, which is hereby incorporated by reference in its entirety, proposes the following classifications for stratifying AKI patients:

"Risk": serum creatinine increased 1.5 fold from baseline OR urine production of <0.5 ml/kg body weight/hr for 6 hours;

"Injury": serum creatinine increased 2.0 fold from baseline OR urine production <0.5 ml/kg/hr for 12 h;

"Failure": serum creatinine increased 3.0 fold from baseline OR creatinine >355 μmol/l (with a rise of >44) or urine output below 0.3 ml/kg/hr for 24 h or anuria for at least 12 hours;

And included two clinical outcomes:

"Loss": persistent need for renal replacement therapy for more than four weeks.

"ESRD": end stage renal disease the need for dialysis for more than 3 months.

These criteria are called the RIFLE criteria, which provide a useful clinical tool to classify renal status. As discussed in Kellum, *Crit. Care Med.* 36: S141-45, 2008 and Ricci et al., *Kidney Int.* 73, 538-546, 2008, each hereby incorporated by reference in its entirety, the RIFLE criteria provide a uniform definition of AKI which has been validated in numerous studies.

More recently, Mehta et al., *Crit. Care* 11:R31 (doi: 10.1186.cc5713), 2007, hereby incorporated by reference in its entirety, proposes the following similar classifications for stratifying AKI patients, which have been modified from RIFLE:

"Stage I": increase in serum creatinine of more than or equal to 0.3 mg/dL (≥26.4 μmol/L) or increase to more than or equal to 150% (1.5-fold) from baseline OR urine output less than 0.5 mL/kg per hour for more than 6 hours;

"Stage II": increase in serum creatinine to more than 200% (>2-fold) from baseline OR urine output less than 0.5 mL/kg per hour for more than 12 hours;

"Stage III": increase in serum creatinine to more than 300% (>3-fold) from baseline OR serum creatinine ≥354 μmol/L accompanied by an acute increase of at least 44 μmol/L OR urine output less than 0.3 mL/kg per hour for 24 hours or anuria for 12 hours.

The CIN Consensus Working Panel (McCollough et al, Rev Cardiovasc Med. 2006; 7(4): 177-197, hereby incorporated by reference in its entirety) uses a serum creatinine rise of 25% to define Contrast induced nephropathy (which is a type of AKI). Although various groups propose slightly different criteria for using serum creatinine to detect AKI, the consensus is that small changes in serum creatinine, such as 0.3 mg/dL or 25%, are sufficient to detect AKI (worsening renal function) and that the magnitude of the serum creatinine change is an indicator of the severity of the AKI and mortality risk.

Recently, a prospective, multicenter investigation in which two novel biomarkers for AKI were identified in a discovery cohort of critically ill adult patients and subsequently validated using a clinical assay and compared to existing markers of AKI in an independent validation cohort of heterogeneous critically ill patients. Urinary insulin-like growth factor binding protein 7 (IGFBP7) and tissue inhibitor of metalloproteinase 2 (TIMP-2) robust markers that have improved performance characteristics when directly compared with existing methods for detecting risk for AKI, but also provide significant additional information over clinical data. It is notable that IGFBP7 and TIMP-2 are each involved with the phenomenon of $G_1$ cell cycle arrest during the very early phases of cell injury, it has been shown that renal tubular cells enter a short period of G1 cell-cycle arrest following injury from experimental sepsis or ischemia. See, e.g., Yang et al., *J. Infect.* 58:459-464, 2009; Witzgall et al., *J. Clin. Invest.* 93:2175-2188, 1994.

(AKI) remains a vexing clinical problem, in part, because it is difficult to identify before there is loss of organ function, which may then become irreversible. Moreover, available therapies are mainly predicated on supportive measures and the removal of nephrotoxic agents. These limitations underscore the need for better methods to detect, assess, and treat AKI, preferably before irreversible injury has occurred.

BRIEF SUMMARY OF THE INVENTION

It is an object of the present invention to provide methods and compositions for protection of subjects from acute kidney injury by treating the subject with compounds that modulate the cell cycle. Modulating the cell cycle can comprise inducing $G_0/G_1$ cell cycle arrest, and/or inducing cell cycle progression. As demonstrated below, even a single administration of a compound which induces $G_0/G_1$ cell cycle arrest can protect subjects from AKI, and may be used prophylactically in advance of, or as a treatment following, various treatments or conditions that are known to be injurious to the kidney, followed optionally by release of the arrest. Once AKI is established, cell cycle progression can be induced to increase replacement of lost and damaged cells.

In certain embodiments, such treatments may be combined with the use of one or more biomarkers which are related to cell cycle state to assess the status of the subject's kidney. These biomarkers can be used to assess the current cell cycle state of the kidney, and may be used to assess improvements in renal status in subjects that have already suffered an acute kidney injury. When urine TIMP-2 and/or IGFBP7 levels are elevated and the presumed exposure that produced AKI is recent (e.g., within 48 hours, preferably within 36 hrs, and still more preferably within 24 hours) inducing $G_0/G_1$ cell cycle arrest may be protective. In contrast, when urine TIMP-2 and/or IGFBP7 levels are elevated and the presumed exposure that produced AKI is distant (>36 hrs) inducers of cell cycle progression may be beneficial by mitigating prolonged cell cycle arrest leading to cell senescence.

By way of example only, treatment of animals with compounds that modulate the cell cycle by inducing $G_0/G_1$ cell cycle arrest such as cyclosporine A can protect or improve the renal status of the animal as measured by plasma creatinine levels. Urine measurements of IGFBP7 and/or TIMP-2 increase initially after cyclosporine A treatment, and then decrease after 24 hrs in animals with a reduced risk of progression to AKI. In contrast, measurements of IGFBP7 and/or TIMP-2 which demonstrate a late increase are shown to be indicative of animals that progress to AKI.

In a first aspect, the present invention relates to methods of prophylactically treating a patient at risk of an acute kidney injury. These methods comprise administering an effective amount of one or more agents that modulate $G_0/G_1$ cell cycle arrest of renal epithelial cells to the patient for a time sufficient to induce cell cycle arrest in a population of the renal epithelial cells but insufficient to induce nephrotoxicity as measured by progression of the patient to acute renal failure.

By way of example only, the one or more agents that modulate $G_0/G_1$ cell cycle arrest may be selected from the group consisting of cyclosporine A, artesunate, Simvastatin, Bufalin, NC381, Flavopiridol, Everolimus, Lycorine, TIMP-2 and IGFBP7. This list is not meant to be limiting. In exemplary embodiments described herein, the one or more agents that modulate $G_0/G_1$ cell cycle arrest comprise, or consist of, cyclosporine A.

In certain embodiments, the subject may also be treated with one or more chemical agents which ameliorate the neprhotoxic effects of the agents that modulate $G_0/G_1$ cell cycle arrest. Preferably, the subject is administered one or more agents which inhibit apoptosis in combination with the one or more agents that modulate $G_0/G_1$ cell cycle arrest. Such one or more agents which inhibit apoptosis comprise or consist of one or more glucocorticoids.

In a second aspect, the present invention relates to methods of treating a patient having an acute kidney injury. These methods comprise administering an effective amount of one or more agents that modulate cell cycle progression of renal epithelial cells to the patient for a time sufficient to induce cell cycle progression in a population of the renal epithelial cells.

By way of example only, the one or more agents that modulate cell cycle progression may be selected from the group consisting of Trametinib, Palifermin, antibodies which bind to and inhibit TIMP-2 and antibodies which bind to and inhibit IGFBP7. This list is not meant to be limiting.

As described hereinafter, use of a cell-cycle arrest modulator together with the biomarkers can offer a new potential treatment modality for acute kidney injury. Thus, in certain embodiments the methods described herein further comprise:
performing a first biomarker assay on a first body fluid sample obtained from the patient which measures IGFBP7 and/or TIMP-2 to provide a first assay result, wherein the first body fluid sample is obtained from the patient prior to the administering step;
performing a second biomarker assay on a body fluid sample obtained from the patient which measures IGFBP7 and/or TIMP-2 to provide a second assay result, wherein the first body fluid sample is obtained from the patient 48 hours following the administering step; and
comparing the first and second assay result.

In certain embodiments, when IGFBP7 levels are increased but TIMP-2 levels are not, inducers of $G_0/G_1$ cell cycle arrest may be protective. Conversely, When TIMP-2 levels are increased but IGFBP7 levels are not, inducers of cell cycle progression may be beneficial.

As discussed above, the methods described herein may be used prophylactically in advance of, or as a treatment following, various treatments or conditions that are known to be injurious to the kidney. Thus, in certain embodiments, the methods may further comprise the subject undergoing vascular surgery, coronary artery bypass, other cardiac surgery, or the administration of one or more radiopaque contrast agents, within 48 hours of the administering step. The subject may be selected based on the pre-existence in the subject of one or more known risk factors for prerenal, intrinsic renal, or postrenal ARF. In certain aspects, the subject has sepsis, and/or the subject is in RIFLE stage 0 or R at the time of the administering step.

Additional clinical indicia of health status, and particularly of renal sufficiency, may be combined with the IGFBP7 and/or TIMP-2 measurements in the methods described herein. Such clinical indicia may include one or more of: a baseline urine output value for the patient, a baseline change in serum creatinine for the patient, demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), other clinical variables (e.g., blood pressure, temperature, respiration rate), risk scores (APACHE score, PREDICT score, TIMI Risk Score for UA/NSTEMI, Framingham Risk Score, risk scores of Thakar et al. (J. Am. Soc. Nephrol. 16: 162-68, 2005), Mehran et al. (J. Am. Coll. Cardiol. 44: 1393-99, 2004), Wijeysundera et al. (JAMA 297: 1801-9, 2007), Goldstein and Chawla (Clin. J. Am. Soc. Nephrol. 5: 943-49, 2010), or Chawla et al. (Kidney Intl. 68: 2274-80, 2005)), a glomerular filtration rate, an estimated glomerular filtration rate, a urine production rate, a serum or plasma creatinine concentration, a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatine ratio, a renal failure index calculated as urine sodium/(urine creatinine/plasma creatinine), a serum or plasma neutrophil gelatinase (NGAL) concentration, a urine NGAL concentration, a serum or plasma cystatin C concentration, a serum or plasma cardiac troponin concentration, a serum or plasma BNP concentration, a serum or plasma NTproBNP concentration, and a serum or plasma proBNP concentration. Other measures of renal function which may be combined with IGFBP7 and/or TIMP-2 assay result(s) are described hereinafter and in Harrison's Principles of Internal Medicine, 17th Ed., McGraw Hill, New York, pages 1741-1830, and Current Medical Diagnosis & Treatment 2008, 47th Ed, McGraw Hill, New York, pages 785-815, each of which are hereby incorporated by reference in their entirety.

Various methods may be used to evaluate the IGFBP7 and/or TIMP-2 biomarker results. By way of example, a cutoff for a biomarker or a combination of biomarkers may be selected which has been predetermined to divide a relevant population into two or more groups. A first group, often called the "nondiseased" population for convenience, represents those patients which have a high risk of AKI. A second group represents those patients with a risk of AKI is small as measured by the biomarker result. A relative risk of AKI for the second group is determined relative to the risk in the first group. A relative risk of 1 means there is no difference in risk between the two groups; while a relative risk of >1 means the risk is higher in the second group.

The ability of a particular test to distinguish two populations can be established using ROC analysis. For example, ROC curves established from a "first" subpopulation which is predisposed to one or more future changes in renal status, and a "second" subpopulation which is not so predisposed can be used to calculate a ROC curve, and the area under the curve provides a measure of the quality of the test. Preferably, the tests described herein provide a ROC curve area greater than 0.5, preferably at least 0.6, more preferably 0.7, still more preferably at least 0.8, even more preferably at least 0.9, and most preferably at least 0.95.

In certain aspects, the measured IGFBP7 and/or TIMP-2 concentrations may be treated as continuous variables. For example, any particular concentration can be converted into a corresponding probability of a future reduction in renal function for the subject, the occurrence of an injury, a classification, etc. In yet another alternative, a threshold that can provide an acceptable level of specificity and sensitivity in separating a population of subjects into "bins" such as a "first" subpopulation (e.g., which is predisposed to one or more future changes in renal status, the occurrence of an injury, a classification, etc.) and a "second" subpopulation which is not so predisposed. A threshold value is selected to separate this first and second population by one or more of the following measures of test accuracy:
- an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;
- a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;
- a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;
- at least about 75% sensitivity, combined with at least about 75% specificity;
- a positive likelihood ratio (calculated as sensitivity/(1-specificity)) of greater than 1, at least about 2, more preferably at least about 3, still more preferably at least about 5, and most preferably at least about 10; or
- a negative likelihood ratio (calculated as (1-sensitivity)/specificity) of less than 1, less than or equal to about 0.5, more preferably less than or equal to about 0.3, and most preferably less than or equal to about 0.1.

The term "about" in the context of any of the above measurements refers to +/−5% of a given measurement.

Multiple thresholds may also be used to assess renal status in a subject. For example, a "first" subpopulation which is predisposed to one or more future changes in renal status, the occurrence of an injury, a classification, etc., and a "second" subpopulation which is not so predisposed can be combined into a single group. This group is then subdivided into three or more equal parts (known as tertiles, quartiles, quintiles, etc., depending on the number of subdivisions). An odds ratio is assigned to subjects based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to suffer one or more future changes in renal status in comparison to someone in the first tertile. The third tertile is also assigned an odds ratio that is relative to that first tertile.

In certain embodiments, the subject is selected for risk stratification based on the pre-existence in the subject of one or more known risk factors for prerenal, intrinsic renal, or postrenal ARF. For example, a subject undergoing or having undergone major vascular surgery, coronary artery bypass, or other cardiac surgery; a subject having pre-existing congestive heart failure, preeclampsia, eclampsia, diabetes mellitus, hypertension, coronary artery disease, proteinuria, renal insufficiency, glomerular filtration below the normal range, cirrhosis, serum creatinine above the normal range, or sepsis; or a subject exposed to NSAIDs, tacrolimus, aminoglycosides, foscarnet, ethylene glycol, hemoglobin, myoglobin, Ifosfamide, heavy metals, methotrexate, radiopaque contrast agents, or streptozotocin are all preferred subjects for monitoring risks according to the methods described herein.

BRIEF DESCRIPTION OF THE FIGURES

FIG. 6A. Plasma creatinine (mean±SE, mg/dl); FIG. 6B. Urine NGAL (mean±SE, U/ml); FIG. 6C. Percentage of different severity of AM measured by RIFLE categories. R, I, F=AM RIFLE classes Risk (creatinine change 150-199%), Injury (creatinine change 200-299%) and Failure (creatinine change >300%). 8/24 (33.33%) in CsA had RIFLE-R, vs 16/24 (66.67%) in vehicle had RIFLE-R (P<0.05).

FIG. 7A. Kaplan-Meier survival curve; FIG. 7B. Association between survival and AM severity.

Eighteen hours after CLP, animals (n=16-24 each group) were randomly assigned to receive either a single dose of CsA or vehicle. All animals received ampicillin/sulbactam starting 18 hours after CLP for three days. Data are expressed as mean±SE*P<0.05, CsA vs Vehicle. FIG. 8A. TIMP-2 (μg/ml); FIG. 8B. IGFBP7 (μg/ml); FIG. 8C. [TIMP-2]x[IGFBP7] (μg2/m12).

Healthy animals (received laparotomy but no CLP, n=6 each group) were randomly assigned to receive either a single dose of CsA or vehicle. FIG. 10A. Plasma IL-6 (mean±SE, pg/ml); FIG. 10B. Plasma creatinine (mean±SE, mg/dl); FIG. 10C. Caspase 3 and Caspase 9 in kidney tissue (mean±SE, OD).

DETAILED DESCRIPTION OF THE INVENTION

Figure 1:
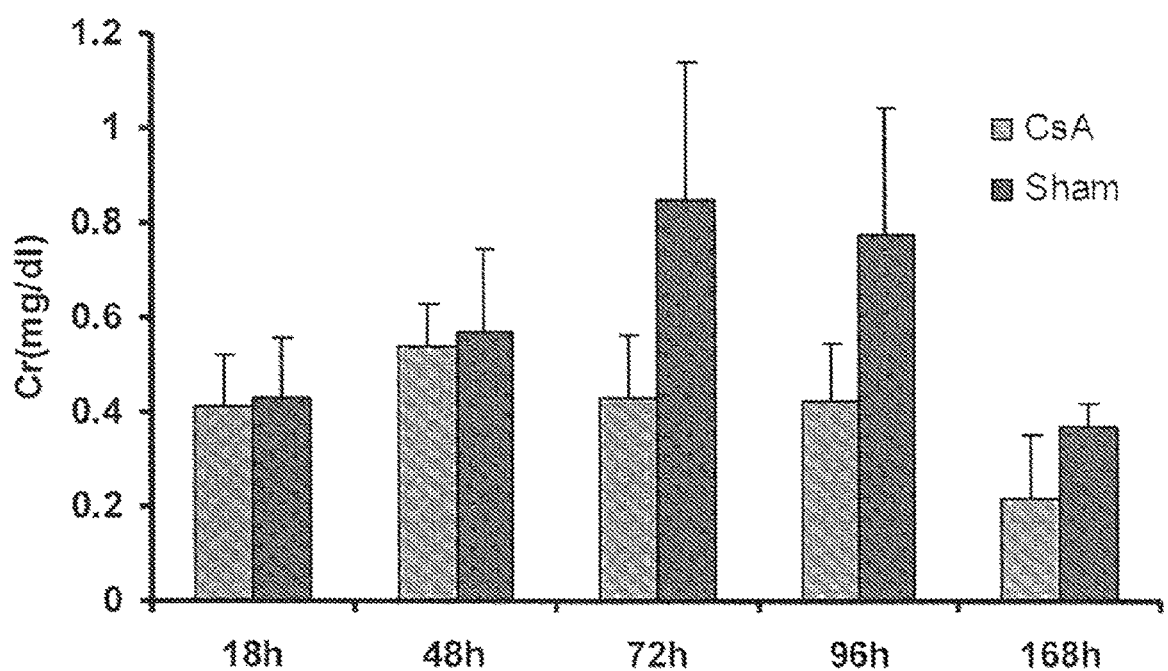
FIG. 1 depicts creatinine levels at various times following CLP.

Acute kidney injury (AKI) is defined as an abrupt or rapid decline in renal filtration function, and is a clinical syndrome that is associated with significant morbidity and mortality. The incidence of AKI has more than doubled in the past decade and is projected to continue to increase. Patients with AKI are cared for by a multitude of specialists including, but not limited to, emergency medicine physicians, internists, pediatricians, surgeons, intensivists, and nephrologists. Patients who develop AKI often require renal replacement therapy (RRT), but clinicians often disagree about the optimal timing of the initiation of RRT.

Measures to correct underlying causes of AKI should begin at the earliest possible time point. Serum creatinine, which is the current bellwether for renal status, does not rise to abnormal levels until a large proportion of the renal mass is damaged, because the relationship between the glomerular filtration rate (GFR) and the serum creatinine level is not linear, especially early in disease. Indeed, the rise of serum creatinine may not be evident before 50% of the GFR is lost. As the current treatment for AKI is mainly supportive in nature (no therapeutic modalities to date have shown efficacy in treating the condition), the ability to prevent AKI would be of tremendous use clinically.

The present invention provides methods and compositions for protection of subjects from acute kidney injury by prophylactically treating the subject with compounds that modulate the cell cycle by inducing $G_0/G_1$ cell cycle arrest. Administration of such a compound can protect subjects from AKI, and may be used in advance of, or following, various treatments or conditions that are known to be injurious to the kidney. These include treatments such as cardiac surgery, including coronary artery bypass grafting (CABG) and surgery for valvular disease (AKI incidence is approximately 30% of patients undergoing cardiac or cardiothoracic surgery; cardiac surgery requiring cardiopulmonary bypass (CPB) is the second most common cause of AKI in the intensive care unit), administration of contrast imaging agents (the third most common cause of new AKI in hospitalized patients), use of non-steroidal anti-inflammatory drugs; and conditions such as sepsis (accounting for 50% or more of cases of AKI in ICUs).

In certain embodiments, such treatments may be combined with the use of one or more biomarkers which are related to cell cycle state to assess the status of the subject's kidney. These biomarkers can be used to assess the current cell cycle state of the kidney, and may be used to assess improvements in renal status in subjects that have already suffered an acute kidney injury.

For purposes of this document, the following definitions apply:

As used herein, an "injury to renal function" is an abrupt (within 14 days, preferably within 7 days, more preferably within 72 hours, and still more preferably within 48 hours) measurable reduction in a measure of renal function. Such an injury may be identified, for example, by a decrease in glomerular filtration rate or estimated GFR, a reduction in urine output, an increase in serum creatinine, an increase in serum cystatin C, a requirement for renal replacement therapy, etc. "Improvement in Renal Function" is an abrupt (within 14 days, preferably within 7 days, more preferably within 72 hours, and still more preferably within 48 hours) measurable increase in a measure of renal function. Preferred methods for measuring and/or estimating GFR are described hereinafter.

As used herein, "reduced renal function" is an abrupt (within 14 days, preferably within 7 days, more preferably within 72 hours, and still more preferably within 48 hours) reduction in kidney function identified by an absolute increase in serum creatinine of greater than or equal to 0.1 mg/dL (≥8.8 µmol/L), a percentage increase in serum creatinine of greater than or equal to 20% (1.2-fold from baseline), or a reduction in urine output (documented oliguria of less than 0.5 ml/kg per hour).

As used herein, "acute renal failure" or "ARF" is an abrupt (within 14 days, preferably within 7 days, more preferably within 72 hours, and still more preferably within 48 hours) reduction in kidney function identified by an absolute increase in serum creatinine of greater than or equal to 0.3 mg/dl (≥26.4 µmol/l), a percentage increase in serum creatinine of greater than or equal to 50% (1.5-fold from baseline), or a reduction in urine output (documented oliguria of less than 0.5 ml/kg per hour for at least 6 hours). This term is synonymous with "acute kidney injury" or "AKI."

"Agent which modulate $G_0/G_1$ arrest" as used herein refers to a chemical agent which, when administered to an animal, induces the percentage of renal epithelial cells in the $G_0/G_1$ stages of the cell cycle to increase. It is not meant that all renal epithelial cells will be found in the $G_0/G_1$ stages. Such agents include, but are not limited to, cyclosporine A, artesunate, Simvastatin, Bufalin, NC381, and Lycorine. Other agents which may be used to modulate $G_0/G_1$ arrest include molecules that affect (directly or indirectly) cyclin-dependent kinases, such as PAMPs (pathogen-associated molecular patterns) and DAMPs (damage-associated molecular patterns).

"Agent which inhibits apoptosis" as used herein refers to a chemical agent which, when administered to an animal, decreases the percentage of renal epithelial cells undergoing apoptosis. It is not meant that no renal epithelial cells will be undergoing apoptosis. Such agents include, but are not limited to, glucocorticoids, interleukin 6 (IL-6), and granulocyte-macrophage colony-stimulating factor.

"Administration" as it is used herein with regard to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell. By "administered together" it is not meant to be implied that two or more agents be administered as a single composition. Although administration as a single composition is contemplated by the present invention, such agents may be delivered to a single subject as separate administrations, which may be at the same or different time, and which may be by the same route or different routes of administration.

"Therapeutically effective amount" is defined as an amount of a reagent or pharmaceutical composition that is sufficient to show a patient benefit, i.e., to cause a decrease, prevention, or amelioration of the symptoms of the condition being treated. When the agent or pharmaceutical composition comprises a diagnostic agent, a "diagnostically effective amount" is defined as an amount that is sufficient to produce a signal, image, or other diagnostic parameter. Effective amounts of the pharmaceutical formulation will vary according to factors such as the degree of susceptibility of the individual, the age, gender, and weight of the individual, and idiosyncratic responses of the individual. "Effective amount" encompasses, without limitation, an amount that can ameliorate, reverse, mitigate, prevent, or diagnose a symptom or sign of a medical condition or disorder or a causative process thereof. Unless dictated otherwise, explicitly or by context, an "effective amount" is not limited to a minimal amount sufficient to ameliorate a condition.

"Treatment" or "treating" (with respect to a condition or a disease) is an approach for obtaining beneficial or desired results including and preferably clinical results. For purposes of this invention, beneficial or desired results with respect to a disease include, but are not limited to, one or more of the following: preventing a disease, improving a condition associated with a disease, curing a disease, lessening severity of a disease, delaying progression of a disease, alleviating one or more symptoms associated with a disease, increasing the quality of life of one suffering from a disease, and/or prolonging survival. Likewise, for purposes of this invention, beneficial or desired results with respect to a condition include, but are not limited to, one or more of the following: preventing a condition, improving a condition, curing a condition, lessening severity of a condition, delaying progression of a condition, alleviating one or more symptoms associated with a condition, increasing the quality of life of one suffering from a condition, and/or prolonging survival. For instance, in embodiments where the compositions described herein are used for treatment of cancer, the beneficial or desired results include, but are not limited to, one or more of the following: reducing the proliferation of (or destroying) neoplastic or cancerous cells, reducing metastasis of neoplastic cells found in cancers, shrinking the size of a tumor, decreasing symptoms resulting from the cancer, increasing the quality of life of those suffering from the cancer, decreasing the dose of other medications required to treat the disease, delaying the progression of the cancer, and/or prolonging survival of patients having cancer. Depending on the context, "treatment" of a subject can imply that the subject is in need of treatment, e.g., in the situation where the subject comprises a disorder expected to be ameliorated by administration of a reagent.

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology.

Preferably, an analyte is measured in a sample. Such a sample may be obtained from a subject, or may be obtained from biological materials intended to be provided to the subject. For example, a sample may be obtained from a kidney being evaluated for possible transplantation into a subject, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the subject from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

Pharmaceutical Compositions

The chemical agents of the present invention (e.g., one or more agents that modulate $G_0/G_1$ cell cycle arrest, one or more agents which inhibit apoptosis, etc.) are preferably provided as pharmaceutical compositions. The term "pharmaceutical" as used herein refers to a chemical substance intended for use in the cure, treatment, or prevention of disease and which is subject to an approval process by the U.S. Food and Drug Administration (or a non-U.S. equivalent thereof) as a prescription or over-the-counter drug product. Details on techniques for formulation and administration of such compositions may be found in Remington, The Science and Practice of Pharmacy 21$^{st}$ Edition (Mack Publishing Co., Easton, Pa.) and Nielloud and Marti- Mestres, Pharmaceutical Emulsions and Suspensions: $2^{nd}$ Edition (Marcel Dekker, Inc, New York).

For the purposes of this disclosure, the pharmaceutical compositions may be administered by a variety of means including orally, parenterally, by inhalation spray, topically, or rectally in formulations containing pharmaceutically acceptable carriers, adjuvants and vehicles. The term parenteral as used here includes but is not limited to subcutaneous, intravenous, intramuscular, intraarterial, intradermal, intrathecal and epidural injections with a variety of infusion techniques. Intraarterial and intravenous injection as used herein includes administration through catheters. Administration via intracoronary stents and intracoronary reservoirs is also contemplated. The term oral as used herein includes, but is not limited to oral ingestion, or delivery by a sublingual or buccal route. Oral administration includes fluid drinks, energy bars, as well as pill formulations.

Pharmaceutical compositions may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing a drug compound in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents; such as magnesium stearate, stearic acid or talc. Tablets may be uncoated, or may be coated by known techniques including enteric coating, colonic coating, or microencapsulation to delay disintegration and adsorption in the gastrointestinal tract and/or provide a sustained action over a longer period. For example, a time delay material such as glyceryl monostearate or glyceryl distearate alone or with a wax may be employed.

Formulations for oral use may be also presented as hard gelatin capsules where the drug compound is mixed with an inert solid diluent, for example calcium phosphate or kaolin, or as soft gelatin capsules wherein the active ingredient is mixed with water or an oil medium, such as peanut oil, liquid paraffin or olive oil.

Pharmaceutical compositions may be formulated as aqueous suspensions in admixture with excipients suitable for the manufacture of aqueous-suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the disclosure may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 20 to 500 mg of active material compounded with an appropriate and convenient amount of carrier material which may vary from about 5 to about 95% of the total compositions. It is preferred that the pharmaceutical composition be prepared which provides easily measurable amounts for administration. Typically, an effective amount to be administered systemically is about 0.1 mg/kg to about 100 mg/kg and depends upon a number of factors including, for example, the age and weight of the subject (e.g., a mammal such as a human), the precise condition requiring treatment and its severity, the route of administration, and will ultimately be at the discretion of the attendant physician or veterinarian. It will be understood, however, that the specific dose level for any particular patient will depend on a variety of factors including the activity of the specific compound employed, the age, body weight, general health, sex and diet of the individual being treated; the time and route of administration; the rate of excretion; other drugs which have previously been administered; and the severity of the particular condition undergoing therapy, as is well understood by those skilled in the art.

As noted above, formulations of the disclosure suitable for oral administration may be presented as discrete units such as capsules, cachets or tablets each containing a predetermined amount of the active ingredient, as a powder or granules; as a solution or a suspension in an aqueous or non-aqueous liquid, or as an oil-in-water liquid emulsion or a water-in-oil liquid emulsion. The pharmaceutical compositions may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropyl ethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made in a suitable machine using a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric or colonic coating to provide release in parts of the gut other than the stomach. This is particularly advantageous with the compounds of formula 1 when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

As used herein, pharmaceutically acceptable salts include, but are not limited to: acetate, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydoxymethyl)aminomethane. Additional pharmaceutically acceptable salts are known to those skilled in the art.

An effective amount for a particular patient may vary depending on factors such as the condition being treated, the overall health of the patient, the route and dose of administration and the severity of side effects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

An effective amount may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of pharmaceutical composition. Where there is more than one administration of a pharmaceutical composition in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice:A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.).

As noted, the compositions of the present invention are preferably formulated as pharmaceutical compositions for parenteral or enteral delivery. A typical pharmaceutical composition for administration to an animal comprises a pharmaceutically acceptable vehicle such as aqueous solutions, non-toxic excipients, including salts, preservatives, buffers and the like. See, e.g., Remington's Pharmaceutical Sciences, 15th Ed., Easton ed. Mack Publishing Co., pp 1405-1412 and 1461-1487 (1975); The National Formulary XIV, 14th Ed., American Pharmaceutical Association, Washington, D.C. (1975). Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to routine skills in the art.

IGFBP7 and TIMP-2 Assays

In general, immunoassays are specific binding assay that involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and The Immunoassay Handbook, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Such assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of IGFBP7 and/or TIMP-2. The kit comprises reagents for the analysis of at least one test sample which comprise at least one antibody that bind each biomarker being assayed. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Antibodies used in the immunoassays described herein preferably specifically bind to a kidney injury marker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{12}$ $M^{-1}$.

Affinity is calculated as $K_d=k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: $r/c=K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

While the present application describes antibody-based binding assays in detail, alternatives to antibodies as binding species in assays are well known in the art. These include receptors for a particular target, aptamers, etc. Aptamers are oligonucleic acid or peptide molecules that bind to a specific target molecule. Aptamers are usually created by selecting them from a large random sequence pool, but natural aptamers also exist. High-affinity aptamers containing modified nucleotides conferring improved characteristics on the ligand, such as improved in vivo stability or improved delivery characteristics. Examples of such modifications include chemical substitutions at the ribose and/or phosphate and/or base positions, and may include amino acid side chain functionalities.

Assay Correlations

The term "correlating" as used herein in reference to the use of biomarkers refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the 97.5th percentile of the concentration seen in a normal population. Another method may be to look at serial samples from the same patient, where a prior "baseline" result is used to monitor for temporal changes in a biomarker level.

Population studies may also be used to select a decision threshold. Receiver Operating Characteristic ("ROC") arose from the field of signal detection theory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1—specificity, the ROC graph is sometimes called the sensitivity vs (1—specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a subject belongs to one classification out of a plurality of classifications.

Measures of test accuracy may be obtained as described in Fischer et al., *Intensive Care Med.* 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1-specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1

Clinical indicia which may be combined with the kidney injury marker assay result(s) of the present invention includes demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a urine total protein measurement, a glomerular filtration rate, an estimated glomerular filtration rate, a urine production rate, a serum or plasma creatinine concentration, a renal papillary antigen 1 (RPA1) measurement; a renal papillary antigen 2 (RPA2) measurement; a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, and/or a renal failure index calculated as urine sodium/(urine creatinine/plasma creatinine). Other measures of renal function which may be combined in the methods of the present invention are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

Combining assay results/clinical indicia in this manner can comprise the use of multivariate logistical regression, loglinear modeling, neural network analysis, n-of-m analysis, decision tree analysis, etc. This list is not meant to be limiting.

Diagnosis of Acute Renal Failure

As noted above, the terms "acute renal (or kidney) injury" and "acute renal (or kidney) failure" as used herein are defined in part in terms of changes in serum creatinine from a baseline value. Most definitions of ARF have common elements, including the use of serum creatinine and, often, urine output. Patients may present with renal dysfunction without an available baseline measure of renal function for use in this comparison. In such an event, one may estimate a baseline serum creatinine value by assuming the patient initially had a normal GFR. Glomerular filtration rate (GFR) is the volume of fluid filtered from the renal (kidney) glomerular capillaries into the Bowman's capsule per unit time. Glomerular filtration rate (GFR) can be calculated by measuring any chemical that has a steady level in the blood, and is freely filtered but neither reabsorbed nor secreted by the kidneys. GFR is typically expressed in units of ml/min:

$$GFR = \frac{\text{Urine Concentration} \times \text{Urine Flow}}{\text{Plasma Concentration}}$$

By normalizing the GFR to the body surface area, a GFR of approximately 75-100 ml/min per 1.73 m$^2$ can be assumed. The rate therefore measured is the quantity of the substance in the urine that originated from a calculable volume of blood.

There are several different techniques used to calculate or estimate the glomerular filtration rate (GFR or eGFR). In clinical practice, however, creatinine clearance is used to measure GFR. Creatinine is produced naturally by the body (creatinine is a metabolite of creatine, which is found in muscle). It is freely filtered by the glomerulus, but also actively secreted by the renal tubules in very small amounts such that creatinine clearance overestimates actual GFR by 10-20%. This margin of error is acceptable considering the ease with which creatinine clearance is measured.

Creatinine clearance (CCr) can be calculated if values for creatinine's urine concentration ($U_{Cr}$), urine flow rate (V), and creatinine's plasma concentration ($P_{Cr}$) are known. Since the product of urine concentration and urine flow rate yields creatinine's excretion rate, creatinine clearance is also said to be its excretion rate ($U_{Cr} \times V$) divided by its plasma concentration. This is commonly represented mathematically as:

$$C_{Cr} = \frac{U_{Cr} \times V}{P_{Cr}}$$

Commonly a 24 hour urine collection is undertaken, from empty-bladder one morning to the contents of the bladder the following morning, with a comparative blood test then taken:

$$C_{Cr} = \frac{U_{Cr} \times 24\text{-hour volume}}{P_{Cr} \times 24 \times 60 \text{ mins}}$$

To allow comparison of results between people of different sizes, the CCr is often corrected for the body surface area (BSA) and expressed compared to the average sized man as ml/min/1.73 m2. While most adults have a BSA that approaches 1.7 (1.6-1.9), extremely obese or slim patients should have their CCr corrected for their actual BSA:

$$C_{Cr-corrected} = \frac{C_{Cr} \times 1.73}{BSA}$$

The accuracy of a creatinine clearance measurement (even when collection is complete) is limited because as glomerular filtration rate (GFR) falls creatinine secretion is increased, and thus the rise in serum creatinine is less. Thus, creatinine excretion is much greater than the filtered load, resulting in a potentially large overestimation of the GFR (as much as a twofold difference). However, for clinical purposes it is important to determine whether renal function is stable or getting worse or better. This is often determined by monitoring serum creatinine alone. Like creatinine clearance, the serum creatinine will not be an accurate reflection of GFR in the non-steady-state condition of ARF. Nonetheless, the degree to which serum creatinine changes from baseline will reflect the change in GFR. Serum creatinine is readily and easily measured and it is specific for renal function.

For purposes of determining urine output on a Urine output on a mL/kg/hr basis, hourly urine collection and measurement is adequate. In the case where, for example, only a cumulative 24-h output was available and no patient weights are provided, minor modifications of the RIFLE urine output criteria have been described. For example, Bagshaw et al., *Nephrol. Dial. Transplant.* 23: 1203-1210, 2008, assumes an average patient weight of 70 kg, and patients are assigned a RIFLE classification based on the following: <35 mL/h (Risk), <21 mL/h (Injury) or <4 mL/h (Failure).

Selecting a Treatment Regimen

Once a diagnosis is obtained, the clinician can readily select a treatment regimen that is compatible with the diagnosis, such as initiating renal replacement therapy, withdrawing delivery of compounds that are known to be damaging to the kidney, kidney transplantation, delaying or avoiding procedures that are known to be damaging to the kidney, modifying diuretic administration, initiating goal directed therapy, etc. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, N J, 1999. In addition, since the methods and compositions described herein provide prognostic information, the markers of the present invention may be used to monitor a course of treatment. For example, improved or worsened prognostic state may indicate that a particular treatment is or is not efficacious.

The distinction between prerenal AKI and instrinsic AKI is an important clinical assessment that directs the therapeutic intervention(s). Patients who are prerenal need therapies directed at hemodynamics to improve renal blood flow. These therapies are often involve inotropes, intravenous fluids and/or vasopressors. Each of these interventions have potential side effects (e.g. arrhythmias, volume overload, vasoconstriction) and would not be advisable to implement these therapies if they are not destined to improve renal function. Thus, the distinction between prerenal AKI and intrinsic AKI helps determine the therapy which should be prescribed. If prerenal AKI is not present, therapy is directed at mitigating AKI and providing supportive care.

Prerenal acute renal failure occurs when a sudden reduction in blood flow to the kidney camera (renal hypoperfusion) causes a loss of kidney function. Causes can include low blood volume, low blood pressure, shunting of blood from the kidney, heart failure, and local changes to the blood vessels supplying the kidney. In prerenal acute renal failure, there is nothing wrong with the kidney itself. Treatment focuses on correcting the cause of the prerenal acute renal failure.

In prerenal AKI without fluid overload, administration of intravenous fluids is typically the first step to improve renal function. This is particularly used in patients in whom prerenal AKI develops as the result of intravascular volume depletion in order to restore normal circulating blood volume. Volume status may be monitored to avoid over- or under-replacement of fluid as described herein. Fluids with colloidal particles such as albumin may be preferred over simple saline infusion. In a prerenal condition wherein the forward flow is compromised, drugs directed at augmenting cardiac output are typically employed.

In patients with congestive heart failure in whom AKI has developed as a result of excessive diuresis, withholding of diuretics and cautious volume replacement may be sufficient to restore kidney function. Inotropes such as norepinephrine and dobutamine may be given to improve cardiac output and hence renal perfusion.

Hospitalized fluid overload patients are typically treated with fluid restriction, IV diuretics, inotropes (e.g., milrinone or dobutamine) and combination therapies. The loop diuretic furosemide is the most frequently prescribed diuretic for treatment of volume overload in HF. Initial oral doses of 20 to 40 mg once a day should be administered to patients with dyspnea on exertion and signs of volume overload who do not have indications for acute hospitalization. Severe overload and pulmonary edema are indications for hospitalization and intravenous furosemide. Some patients with mild HF can be treated effectively with thiazide diuretics. Those who have persistent volume overload on a thiazide diuretic should be switched to an oral loop diuretic. In patients with severe kidney injury, diuretics may not result in significant diuresis. Ultrafiltration, also called aquapheresis, may be used to treat fluid overload in such cases.

In contrast to prerenal AKI, the main goal of treatment of acute tubular necrosis (ATN) is to prevent further injury to the kidney. Ischemic ATN can be caused when the kidneys are not sufficiently perfused for a long period of time (e.g. due to renal artery stenosis) or by shock. Sepsis causes 30% to 70% of deaths in patients with ATN; therefore, avoidance of intravenous lines, bladder catheters, and respirators is recommended. Because septic patients are vasodilated, large volumes of administered fluid accumulate in the lung interstitium of these patients. Extracellular fluid volume should be assessed promptly, and repletion of any deficit should be initiated promptly. Hemodynamic status should be modified by appropriate fluid therapy, giving vasopressors and/or inotropes and treating any underlying sepsis. All possible nephrotoxic drugs should be stopped. In addition, doses of all medications that are eliminated by the kidney should be adjusted.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

Example 1

It has previously been shown that one dose (1 and 5 mg/kg body weight) of cyclosporine A (CsA) following the induction of an injury by administration of folic acid significantly reduced kidney tubular cell apoptosis, serum creatinine, blood urea, serum IL-6 and urinary NGAL 2 days after folic acid-induced AKI in mice. See, e.g., Wen et al., Nephrol. Dial. Transplant. 27: 3100-109, 2012.

In the present study, sepsis was induced by cecal ligation and puncture (CLP) in adult SD rats. Eighteen hours after CLP, rats were randomized to receive either CsA (5 mg/kg) or vehicle (n=12 each) as a single dose via the central vein. At the same time, all animals received ampicillin/sulbactam (125 mg/kg every 12 hrs) as supportive therapy, which was continued for three days.

Blood and urine were taken for measurement of plasma creatinine (Cr), urine neutrophil gelatinase-associated lipocalin (NGAL), urine insulin-like growth factor-binding protein 7 (IGFBP7) and urine tissue inhibitor of metalloproteinases-2 (TIMP-2). Plasma Cr concentrations were increased after CLP and the changes were similar in both groups before intervention. Acute Kidney Injury severity was assessed with RIFLE criteria based on the change in SCr: R (Risk)=SCr increases>50%; I (Injury)=SCr increases>100%; F (Failure)=SCr increases>200%. Survival time was also measured up to 7 days.

After two days of CsA treatments, the plasma Cr began to decrease, while Cr continued to increase in controls (0.43±0.13 vs 0.85±0.28 mg/dl, $p<0.05$). Changes in urine NGAL with time were similar to those of plasma Cr but increased earlier (5852±50 vs 3702±114 IU/ml after 24 hrs of treatment, $p<0.05$). Compared to sham (vehicle) treated animals animals treated with CsA showed significantly higher serum creatinine at 72 and 96 h ($P<0.05$) (FIG. 1). Animals treated with CsA also had significantly decreased AKI severity (AKI-I/F 32% vs 68%), compared to sham (P<0.05). Survival to 7 days was not significantly affected by CsA in this small sample size.

Figure 3:
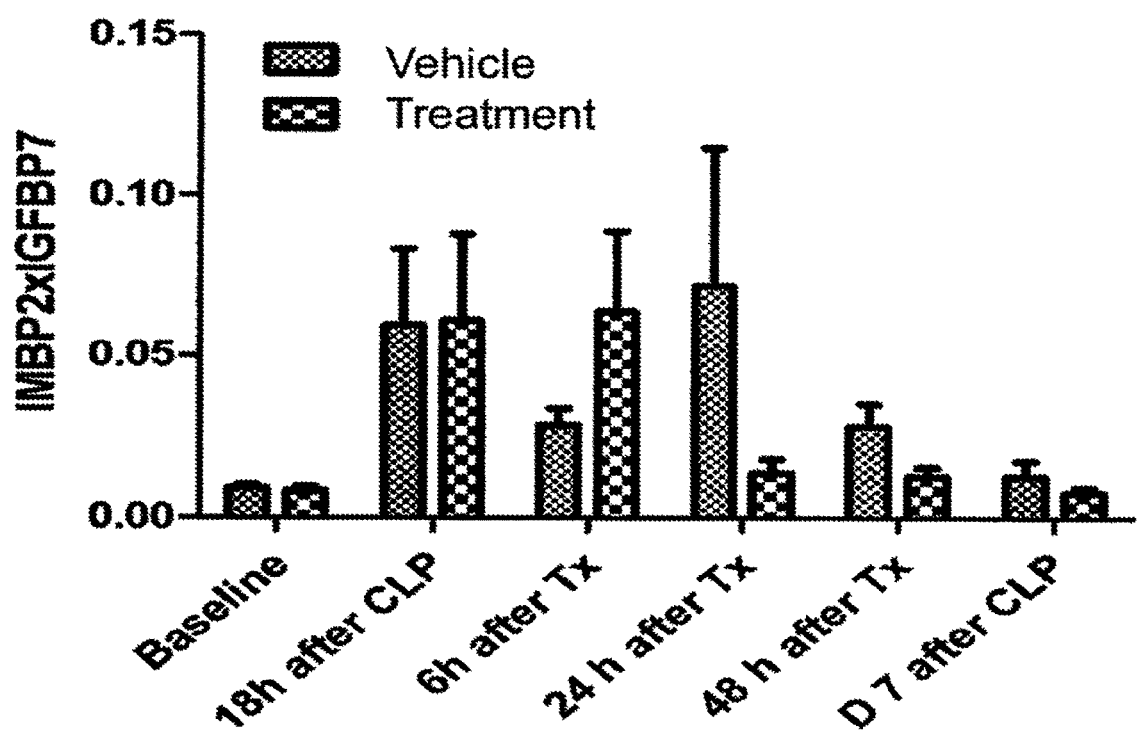
FIG. 3 depicts [TIMP2]×[IGFBP7] at various times following CLP.
Figure 4A:
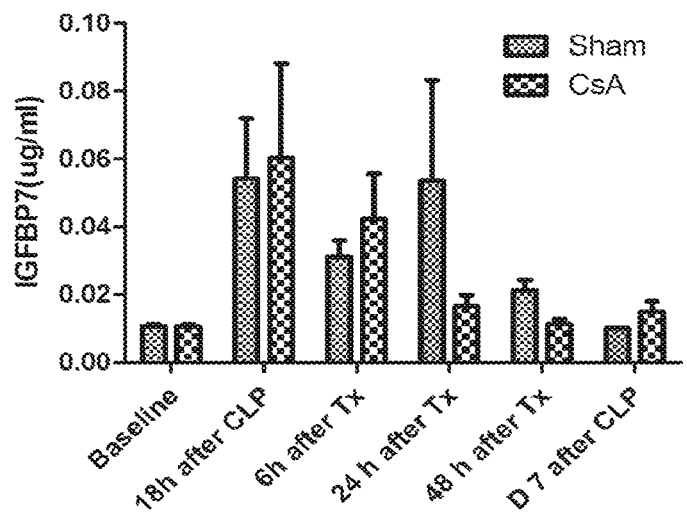
FIG. 4A depicts [IGFBP7] at various times following CLP.
Figure 4B:
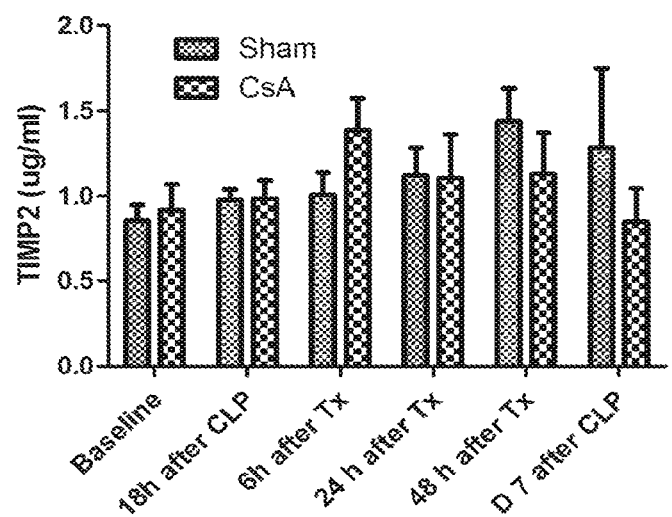
FIG. 4B depicts [TIMP2] at various times following CLP.

TIMP-2 and IGFBP7 measurements were combined into a single composite score as [TIMP-2]×[IGFBP7] as described in Kashani et al., Critical Care 2013, 17:R25 doi:10.1186/cc12503. All animals exhibited an increased expression of the composite score 18 hrs after CLP. In animals receiving CsA urine biomarkers for cell cycle arrest, IGFBP7 and TIMP-2, increased 6 hrs after treatment, and then decreased after 24 hrs. By contrast, control animals exhibited a late increase in biomarkers that heralded AKI, Urinary [(TIMP-2)×(IGFBP7)] was significantly different between groups (0.064±0.01 vs 0.028±0.002) at 6 hrs after treatment; and after 24 hours (0.014±0.001 vs 0.072±0.020), P<0.05) (FIGS. 3 and 4).

These data combined with the effects on kidney injury presented above suggest that inducing cell-cycle arrest using CsA can protect against "naturally occurring" cell-cycle arrest that heralds acute kidney injury. The data also demonstrate that use of a cell-cycle arrest modulator together with the biomarkers can offer a new potential treatment modality for acute kidney injury.

Example 2

The following example describes an exemplary use of biomarkers according to the present invention. A patient is admitted to the hospital with pneumonia. Serum creatinine levels are initially normal but a combined TIMP-2 and IGFBP7 score (calculated as [TIMP-2]×[IGFBP7] levels is elevated. Because the patient has been sick for <36 hrs, the injury is presumed to be recent. Individually, IGFBP7 levels are increased but TIMP-2 levels are normal. The patient is given one dose of cyclosporine A and his serum creatinine levels remain low.

A second patient is also admitted with pneumonia. This time it is unclear how long the illness has been evolving and serum creatinine is slightly elevated on presentation. Individually, TIMP-2 and IGFBP7 levels are both elevated, so cyclosporine is not indicated. The next day, serum creatinine is further elevated and on the following day creatinine reaches twice the baseline level. TIMP2 levels remain increased but IGFBP7 levels have returned to normal. At this point he is given an inducer of cell cycle progression.

Example 3

The purpose of this study was to determine whether CsA treatment, with antibiotics, could attenuate AKI following cecal ligation and puncture (CLP) in rats and to characterize the effects on markers of inflammation, apoptosis, and cell cycle arrest.

72 adult (24 to 28 weeks old, weight 400-600 g), healthy, male, Sprague-Dawley rats were anesthetized by inhalation of isoflurane. Cecal ligation and puncture (CLP) was performed with a predetermined 33% ligated length of cecum and 18-gauge needle: three punctures inferior to the ileocecal valve. The abdomen was closed and 20 ml/kg of normal saline was given subcutaneously for resuscitation. Topical anesthetic was applied to the surgical wound and rats were returned to their cages and allowed food and water ad libitum.

Eighteen hours after CLP, animals were returned to the laboratory and randomly assigned to either one dose (5 mg/kg) of CsA (Sigma-Aldrich, St Louis, Mich.) or vehicle intravenously (n=24 each). All animals received ampicillin/sulbactam (150 mg/kg every 12 hours) starting 18 hours after CLP and continued for three days. A central vein catheter was also placed to draw blood and survival time was assessed up to 7 days. In a separate study, animals were sacrificed either 6 or 24 hours after treatments and kidney tissue was collected for further analysis (n=6 each). In order to exclude any possible effects of cyclosporine on measures of renal function, we gave the same dose of CsA or vehicles to another 12 healthy (laparotomy but no CLP) animals as a control and obtained the same measurements (n=6 each).

Blood (0.8 ml) was drawn from a central venous catheter at 0, 18, 24 (6 hours after treatment), 42 (24 hours after treatment), and 66 hours (48 hours after treatment) after CLP. Urine samples (1-2 ml) were obtained from the bladder at the same time points. Plasma was separated by centrifugation and kept at −80° for subsequent interleukin (IL)-6 and creatinine measurements using an enzyme-linked immunosorbent assay (ELISA) (R & D Systems, Minneapolis, Minn.) and an enzymatic assay kit (BioVision Technologies, Mountain View, Calif.) respectively. Urine samples were analyzed for neutrophil gelatinase-associated lipocalin (NGAL) using a commercial ELISA (BioPorto Diagnostics, Gentofte, Denmark), and tissue inhibitor of metalloproteinases-2 (TIMP-2) and insulin-like growth factor-binding protein 7 (IGFBP7) using a custom ELISA provided by Astute Medical (San Diego, Calif.). Survival time was recorded in days starting from CLP.

The presence and severity of AKI was assessed using the serum creatinine portion of the RIFLE criteria (13), which classifies risk (R), injury (I), and failure (F), on the basis of maximum creatinine increase of 150%, 200% and 300% respectively over the 7 days following CLP.

Renal Caspase 3 and Caspase 9 were measured using a colorimetric method. Briefly, rat kidneys were rinsed in a 0.9% saline bath and dissected to obtain a 100 mg cross section. The 100 mg kidney sample was homogenized and spun in a centrifuge to pellet out the fibrous tissue. The supernatant was then collected and the protein concentration determined by Pierce BCA Protein Assay (Thermo Scientific: 23227, Rockford, Ill.). Using the values acquired from the Pierce BCA Protein Assay, the lysates were diluted with Cell Lysis Buffer to 100-200 ug per 100 uL. Caspase-3 (Bio Vision: K113-100, Milpitas, Calif.) and Caspase-9 (BioVision: K119-100, Milpitas, Calif.) assays were then prepared using the diluted samples according to the recommended procedure. Absorbance was read using a BioTek Synergy HT Multi-Detection Microplate Reader set to 405 nm, analyzed using the associated Gen5 software, and indexed by the tissue weight.

Descriptive data were expressed as means±standard error (SE). The analysis of variance for repeated measures was applied to compare variables under different interventions at different time points. Mann-Whitney U-test was used to compare the non-normally distributed data between two groups. Categorical variables were expressed as proportions and compared using the Chi-square test. The survival analysis was assessed by Kaplan-Meier statistics and compared using Log rank test. Our primary endpoint was the proportion of severe AKI (RIFLE-F) between groups treated with CsA and vehicle. Sample size was based on the primary outcome and was set at 24 animals per group in order to detect an approximate 30-40% change in the rate of RIFLE-F AKI. A two sided P<0.05 was considered statistically significant.

Figure 2:
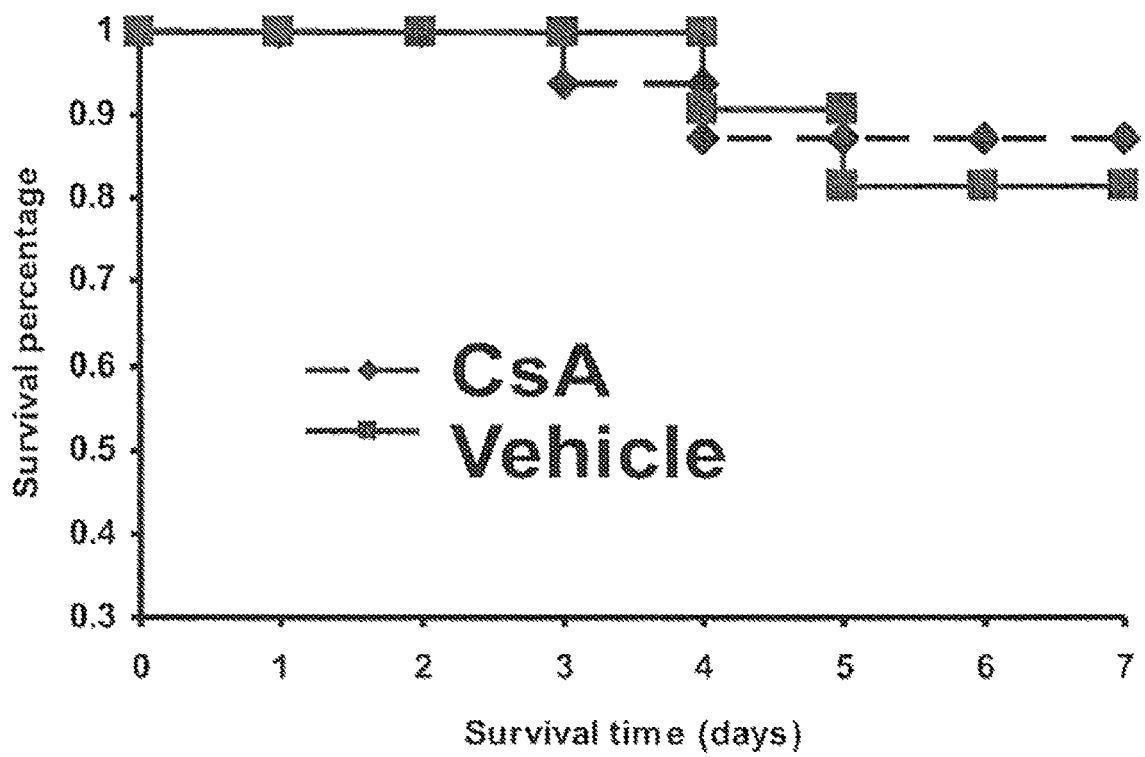
FIG. 2 depicts survival at various times following CLP.
Figure 5:
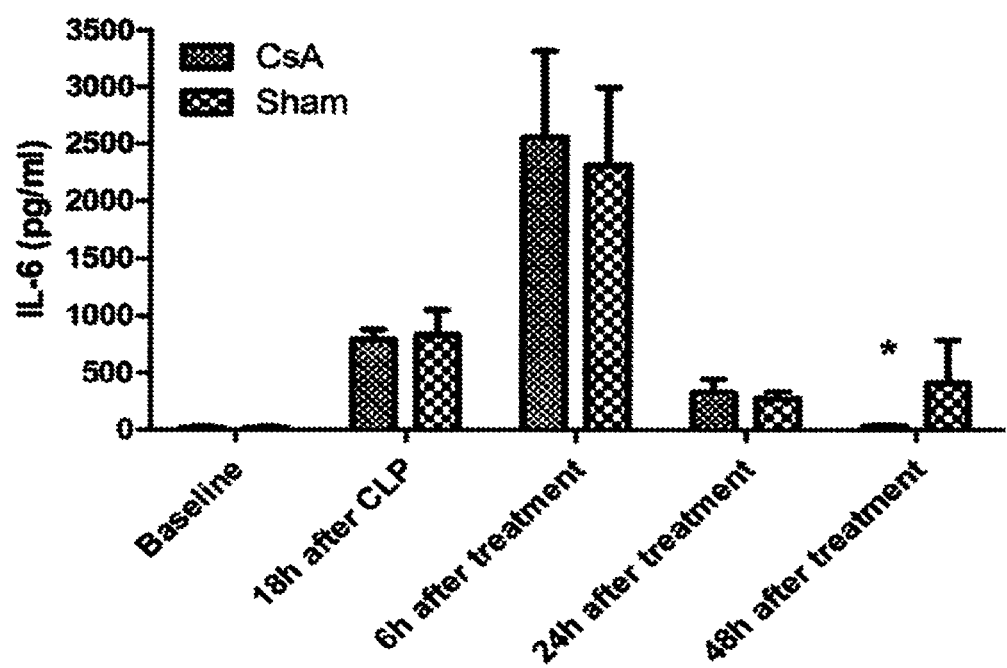
FIG. 5 depicts Effects of cyclosporine A (CsA) on plasma interleukin (IL)-6 in septic rats. Eighteen hours after CLP, animals (n=16-24 each group) were randomly assigned to receive either a single dose of CsA or vehicle. All animals received ampicillin/sulbactam starting 18 hours after CLP for three days.*P<0.05, CsA vs Vehicle (data are expressed as mean±SE, pg/ml).
Figure 6A:
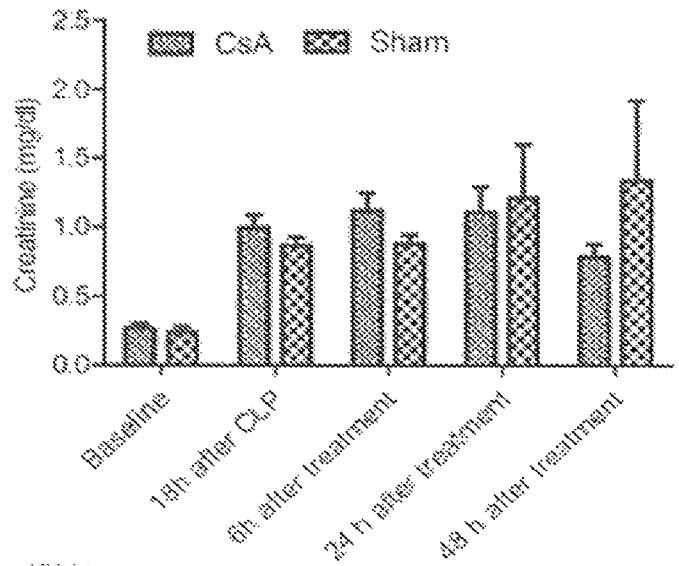
FIGS. 6A-6C depict effects of a single dose of CsA on kidney function in septic rats. Eighteen hours after CLP, animals (n=16-24 each group) were randomly assigned to receive either a single dose of CsA or vehicle. All animals received ampicillin/sulbactam starting 18 hours after CLP for three days. *P<0.05, CsA vs Vehicle.
Figure 6B:
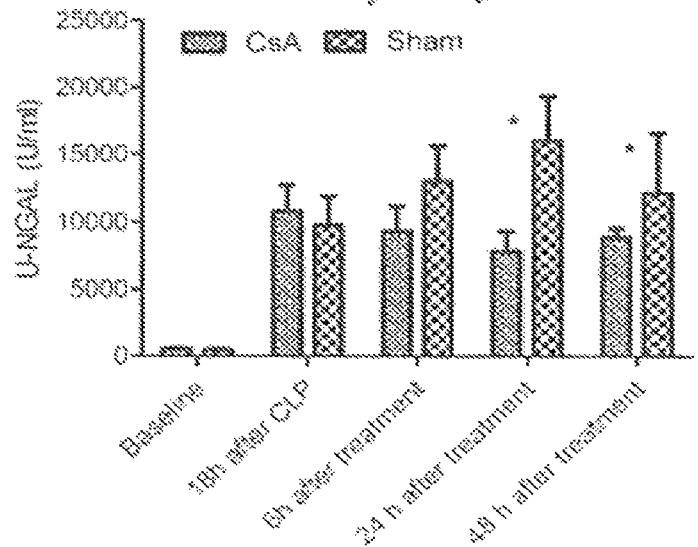
Figure 6C:
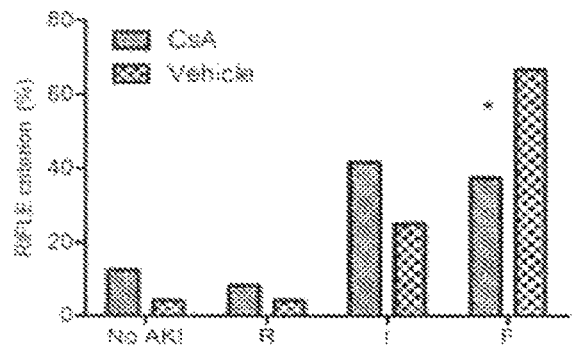

Plasma IL-6 levels increased after CLP, and continuously increased 6 hours after CsA (or vehicle) with antibiotics. However, plasma IL-6 was significantly lower with CsA compared to vehicle 48 hours after treatment ((28.46 vs 407.53 pg/ml, FIG. 5, p<0.001). Severe AKI (RIFLE-F) was nearly twice as likely in animals receiving vehicle (66.7% vs 33.3%, Relative Risk 1.63, 95% CI: 1.17-1.99, p<0.05, FIG. 2). Plasma creatinine increased after CLP in both groups. However, at 48 hours after treatment, creatinine concentrations were significantly lower in CsA-treated animals compared to those receiving vehicle. Changes in urine NGAL were similar to those of plasma creatinine, but NGAL levels were significantly lower with CsA as early as 24 hours after treatment (7849 vs 16049 IU/ml, p<0.05, FIG. 6).

Figure 7A:
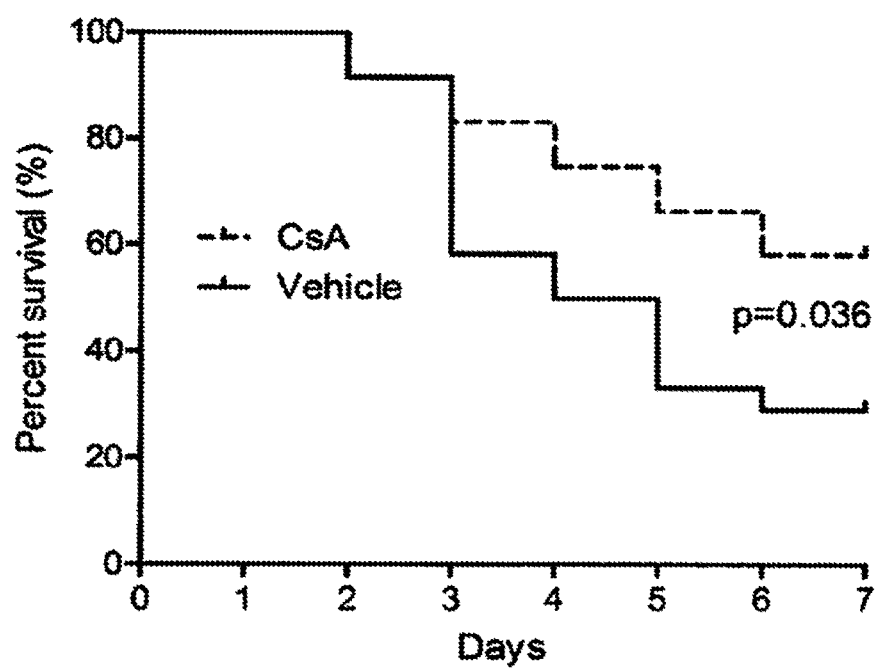
FIGS. 7A-7B depict effects of a single dose of CsA on one-week survival in septic rats. Eighteen hours after CLP, animals (n=16-24 each group) were randomly assigned to receive either a single dose of CsA or vehicle. All animals received ampicillin/sulbactam starting 18 hours after CLP for three days. Survival time was assessed up to seven days.
Figure 7B:
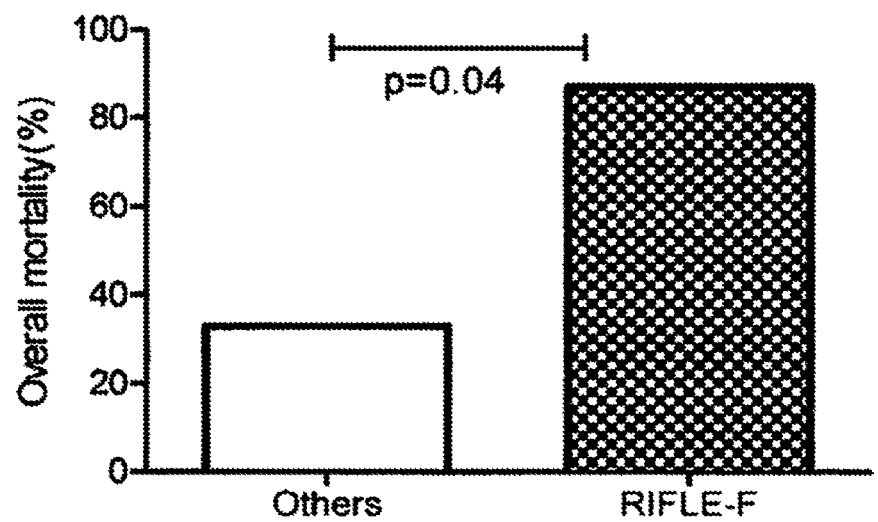

Survival to seven days after CLP (150 hours after treatment) favored CsA treatment (54.17% vs 29.17%, p=0.04, as did survival time; hazard ratio: 0.41, 95% CI: 0.18-0.94, P=0.03, FIG. 7A). When we compared the survival rates and severity of AKI, we found that only 13% of animals with RIFLE-F survived while 67% of the remaining animals survived (FIG. 7B, P<0.05).

Figure 8A:
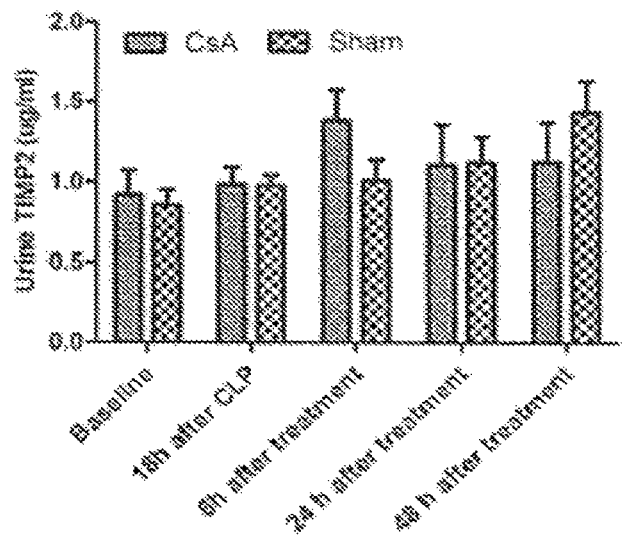
FIGS. 8A-8C depict effects of CsA on urine biomarkers of cell-cycle arrest in septic rats.
Figure 8B:
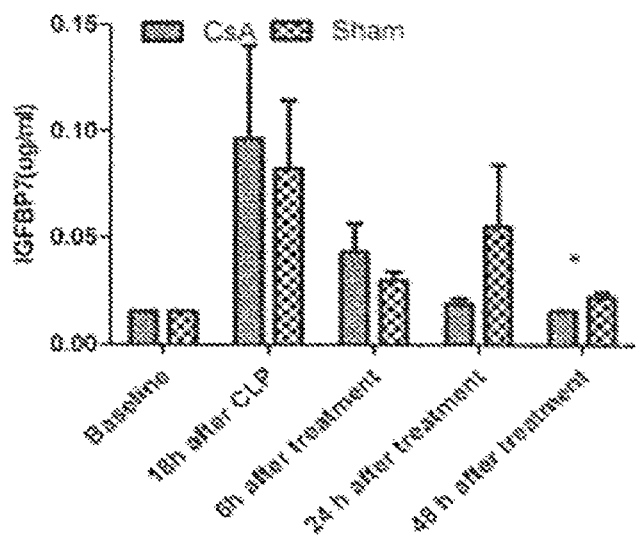
Figure 8C:
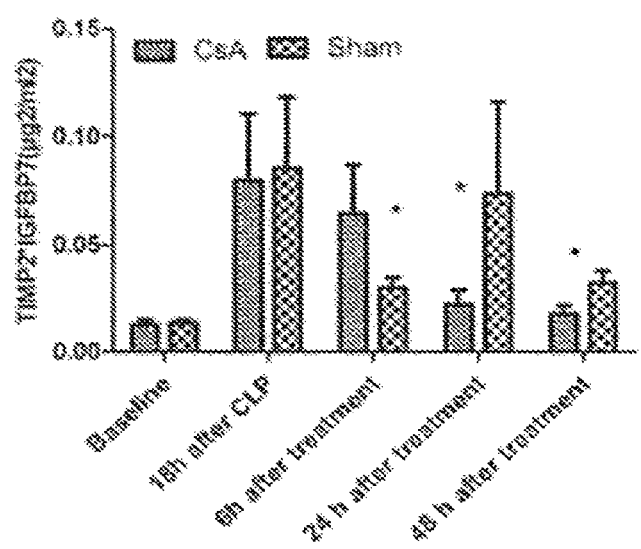
Figure 9:
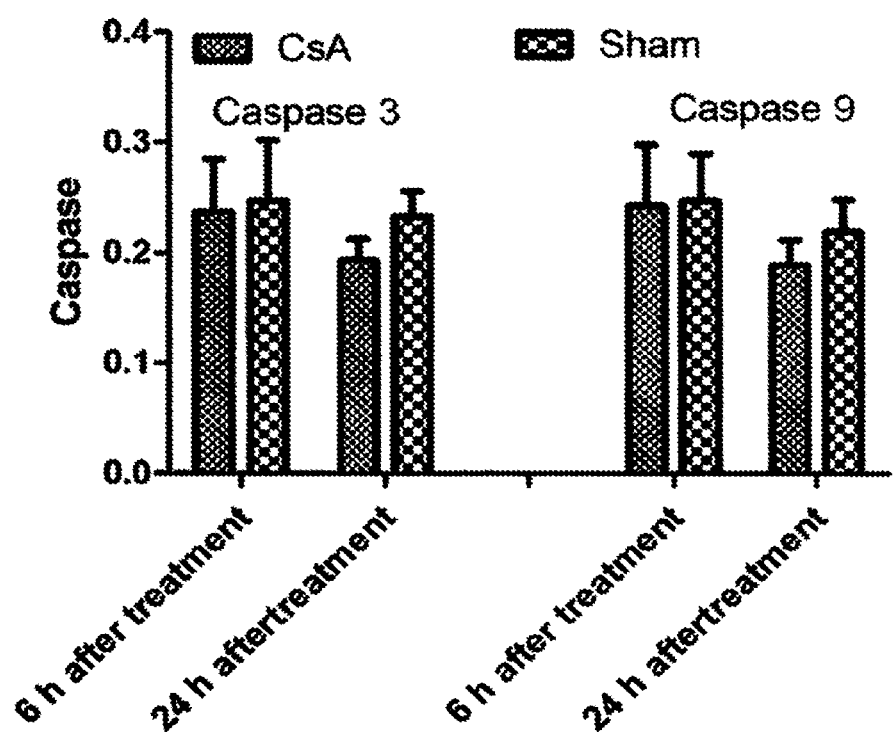
FIG. 9 depicts Effects of a single dose of CsA on apoptosis in kidney tissue in septic rats. Eighteen hours after CLP, animals (n=6 each group) were randomly assigned to receive either a single dose of CsA or vehicle. All animals received ampicillin/sulbactam starting 18 hours after CLP. Animals were sacrificed either 6 or 24 hours after treatments and kidney tissue was collected for measurements of caspase 3 and casepase 9 (data are expressed as mean±SE).

The effects of CsA on [TIMP-2], [IGFBP7] and [TIMP-2]·[IGFBP7] are shown in FIG. 8. Urine [TIMP-2]·[IGFBP7] increased in both groups after CLP. However, CsA resulted in higher [TIMP-2]·[IGFBP7] at 6 hours compared to vehicle p<0.05, but decreased concentrations were observed starting from 24 hours after treatment, (p<0.05, FIG. 8). To explore other mechanisms for the renal protective effects of CsA, we measured caspases 3 and 9 in kidney tissue 6 and 24 hours after treatment. CsA did not alter tissue caspases, (FIG. 9).

Figure 10A:
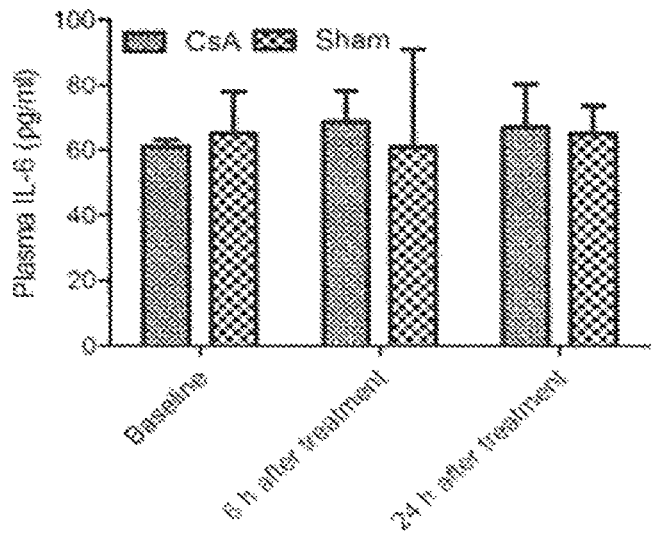
FIGS. 10A-10C depict effects of a single dose of CsA on kidney function in healthy rats.
Figure 10B:
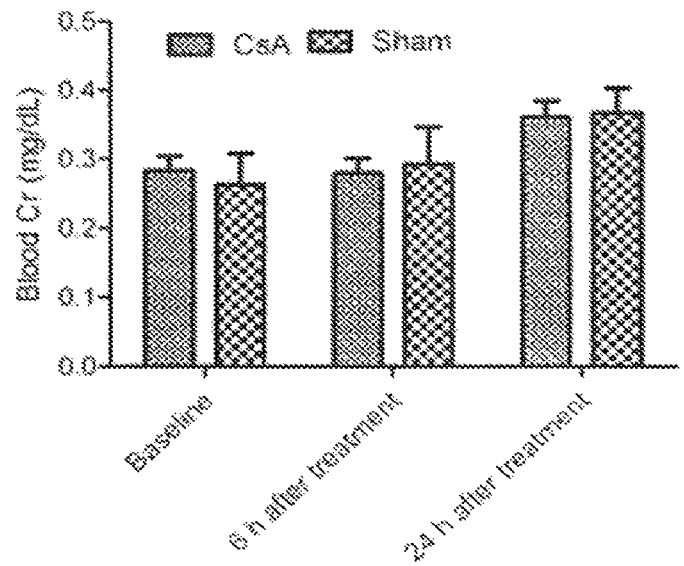
Figure 10C:
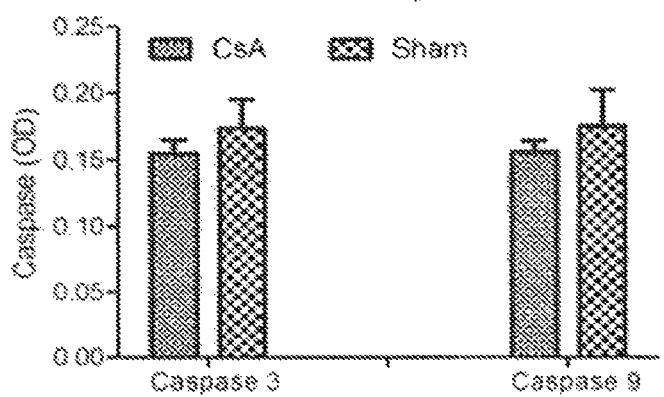

To exclude the possible nephrotoxic effects of CsA in healthy animals, we performed the same measurements in healthy rats. There were small changes in plasma IL-6, creatinine and tissue caspase 3 and 9, but there were no significant differences with time or between CsA and vehicle (p>0.05, FIG. 10).

These results demonstrate that a single dose of CsA attenuated sepsis induced AKI, as evidenced by fewer animals reaching RIFLE-F based plasma creatinine criteria as well as by urine biomarkers. Additionally, a single dose of CsA reduced the inflammatory response as measured by IL-6, and improved a one-week survival. Interestingly, we found that CsA increased cell-cycle arrest biomarkers [TIMP-2]·[IGFBP7]) early on, but decreased these markers (along with reducing severe AKI) later. Finally, CsA did not decreased renal cell apoptosis as measured by caspases 3 and 9.

CsA attenuated AKI as evidenced by a reduced rate of RIFLE-F, as well as by lower urine biomarker concentrations. Importantly, both [TIMP-2]·[IGFBP7] and NGAL increased 24 hours in advance of serum creatinine consistent with multiple other studies. CsA resulted in less inflammation as determined by plasma IL-6. We chose IL-6, as this marker is a common pro-inflammatory mediator and is easily detected in both natural and experimental sepsis. Conversely, urinary [TIMP-2]·[IGFBP7] was significantly greater with CsA six hours after treatment. Induction of $G_1$ cell-cycle arrest, while associated with increased risk for AKI in the subsequent 12-24 hours, is nonetheless a protective mechanism to avoid the cell entering the cell-cycle when it is injured or even in an adverse environment. Thus, an early increase in [TIMP-2]·[IGFBP7] would be expected to be associated with less AKI. This is indeed what was observed. However, we also observed an even greater increase in [TIMP-2]·[IGFBP7] in both groups after CLP and prior to treatment. In order to further characterize the response [TIMP-2] and [IGFBP7] were determined individually (FIG. 8). An early increase (with CLP alone) was only seen with [IGFBP7] not [TIMP-2]. Furthermore, both molecules exhibited a non-significant trend toward higher expression in the CsA group at 6 hours (resulting in a significant difference when the two markers were multiplies together).

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method for detecting one or more kidney injury markers in a subject, the method comprising:
    obtaining a body fluid sample collected from the subject within about 12 hours following a prophylactic treatment for acute kidney injury that uses cyclosporine A to induce $G_0/G_1$ cell cycle arrest of renal epithelial cells; and
    performing an assay on the body fluid sample, wherein the assay measures a concentration of one or more biomarkers to provide an assay result, wherein the one or more biomarkers consists of tissue inhibitor of metalloproteinases 2 (TIMP2) and wherein if the assay result is at least about 30% greater than a control level, the prophylactic treatment was successful.

2. The method according to claim 1, wherein the prophylactic treatment uses one or more agents that inhibit apoptosis in combination with the cyclosporine A.

3. The method according to claim 2, wherein the one or more agents that inhibit apoptosis comprise one or more glucocorticoids.

4. The method according to claim 1, wherein the subject was selected for prophylactic treatment based on a pre-existence in the subject of one or more known risk factors for prerenal, intrinsic renal, or postrenal acute kidney injury.

5. The method according to claim 1, wherein the subject was in RIFLE stage 0 or R at the time of the prophylactic treatment.

6. The method according to claim 1, wherein the subject has sepsis.

7. The method according to claim 1, wherein the body fluid sample is a urine sample.

8. The method according to claim 1, wherein the prophylactic treatment was administered within 48 hours following an exposure to risk of kidney injury.

9. The method according to claim 1, wherein the prophylactic treatment was in advance of an exposure to risk of kidney injury.

10. The method according to claim 1, wherein the body fluid sample is obtained from the subject at about 6 hours after the prophylactic treatment.

11. A method for prophylactically treating a subject at risk of acute kidney injury and detecting one or more kidney injury markers in the prophylactically treated subject, the method comprising:

administering a prophylactic treatment comprising cyclosporine A to induce $G_0/G_1$ cell cycle arrest of renal epithelial cells to the subject;

obtaining a body fluid sample collected from the subject within about 12 hours following the prophylactic treatment; and performing an assay on the body fluid which measures a concentration of one or more biomarkers to provide an assay result, wherein the one or more biomarkers consists of tissue inhibitor of metalloproteinases 2 (TIMP2) and wherein if the assay result is at least about 30% greater than a control level, the prophylactic treatment was successful.

12. The method according to claim 11, wherein the prophylactic treatment is administered within 48 hours following an exposure to risk of kidney injury.

13. The method according to claim 11, wherein the prophylactic treatment is administered in advance of an exposure to risk of kidney injury.

14. The method of claim 13, further comprising determining that the prophylactic treatment was successful prior to the exposure to risk of kidney injury.

15. The method of claim 14, wherein the exposure to risk of kidney injury is an intervention, the method further comprising performing the intervention on the subject within about 48 hours after the prophylactic treatment, wherein the intervention comprises cardiac or vascular surgery or administering a nephrotoxic agent.

16. The method according to claim 11, wherein the body fluid sample is obtained from the subject at about 6 hours after the prophylactic treatment.

* * * * *